United States Patent
Gaspard et al.

(10) Patent No.: US 11,351,214 B2
(45) Date of Patent: Jun. 7, 2022

(54) METHODS FOR MAKING YERBA MATE EXTRACT COMPOSITION

(71) Applicant: CARGILL, INCORPORATED, Wayzata, MN (US)

(72) Inventors: Dan S. Gaspard, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/374,894

(22) Filed: Apr. 4, 2019

(65) Prior Publication Data
US 2019/0231834 A1    Aug. 1, 2019

Related U.S. Application Data

(63) Continuation of application No. PCT/US2018/054688, filed on Oct. 5, 2018.

(60) Provisional application No. 62/569,279, filed on Oct. 6, 2017, provisional application No. 62/676,722, filed on May 25, 2018.

(51) Int. Cl.
| | |
|---|---|
| A61K 36/28 | (2006.01) |
| A23L 27/00 | (2016.01) |
| C07K 1/18 | (2006.01) |
| A23L 27/30 | (2016.01) |
| A23L 5/40 | (2016.01) |
| A23F 3/34 | (2006.01) |
| A23L 2/56 | (2006.01) |
| A23L 2/60 | (2006.01) |
| A23L 2/68 | (2006.01) |
| A61K 31/192 | (2006.01) |
| A61K 31/235 | (2006.01) |
| B01D 15/36 | (2006.01) |
| C07H 15/256 | (2006.01) |
| C07K 1/16 | (2006.01) |

(52) U.S. Cl.
CPC .............. *A61K 36/28* (2013.01); *A23F 3/34* (2013.01); *A23L 2/56* (2013.01); *A23L 2/60* (2013.01); *A23L 2/68* (2013.01); *A23L 5/40* (2016.08); *A23L 27/30* (2016.08); *A23L 27/36* (2016.08); *A23L 27/39* (2016.08); *A23L 27/88* (2016.08); *A61K 31/192* (2013.01); *A61K 31/235* (2013.01); *B01D 15/361* (2013.01); *C07H 15/256* (2013.01); *C07K 1/16* (2013.01); *C07K 1/18* (2013.01); *A23V 2002/00* (2013.01); *A23V 2200/15* (2013.01); *A23V 2250/258* (2013.01); *A61K 2236/31* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 4,872,987 | A | 10/1989 | Kopsch |
| 4,892,938 | A | 1/1990 | Giovanetto |
| 5,888,549 | A | 3/1999 | Buchholz |
| 5,972,120 | A | 10/1999 | Kutowy |
| 6,337,095 | B1 | 1/2002 | Jain |
| 7,279,184 | B2 | 10/2007 | Gow et al. |
| 7,291,352 | B2 | 11/2007 | Gow et al. |
| 7,294,353 | B2 | 11/2007 | Gow et al. |
| 7,651,717 | B2 | 1/2010 | Shioya |
| 7,750,053 | B2 | 7/2010 | Suzuki |
| 7,767,238 | B2 | 8/2010 | Roy |
| 7,838,044 | B2 | 11/2010 | Abelyan |
| 7,939,563 | B2 | 5/2011 | Suzuki |
| 8,088,428 | B2 | 1/2012 | Yamane |
| 8,178,148 | B2 | 5/2012 | Fujii |
| 8,197,875 | B2 | 6/2012 | Chien |
| 8,241,680 | B2 | 8/2012 | Williams |
| 8,293,302 | B2 | 10/2012 | Abelyan |
| 8,337,929 | B2 | 12/2012 | Ogura |
| 8,530,527 | B2 | 9/2013 | Markosyan |
| 8,586,106 | B2 | 11/2013 | Ya et al. |
| 8,728,545 | B2 | 5/2014 | Chabot et al. |
| 9,133,229 | B2 | 9/2015 | Lee |
| 9,358,264 | B2 | 6/2016 | Ibarra |
| 9,457,009 | B2 | 10/2016 | Guthrie |
| 9,510,611 | B2 | 12/2016 | Purkayastha |
| 9,636,373 | B1 | 5/2017 | Akao |
| 9,775,822 | B2 | 10/2017 | Prasad |
| 9,844,576 | B2 | 12/2017 | Brownell |
| 9,848,624 | B2 | 12/2017 | Ley |
| 9,889,107 | B2 | 2/2018 | Guthrie |
| 9,962,356 | B2 | 5/2018 | Prasad |
| 10,188,125 | B2 | 1/2019 | Ozato |
| 10,376,521 | B2 | 8/2019 | Zaworotko |

(Continued)

FOREIGN PATENT DOCUMENTS

| | | |
|---|---|---|
| CN | 1100894 A | 4/1995 |
| CN | 1336333 A | 2/2002 |

(Continued)

OTHER PUBLICATIONS

Deladino et al. (2013) Food and Nutrition Sciences 4: 154-162. (Year: 2013).*
Berte et al. (2011) J. Agric. Food Chem. 59: 5523-5527. (Year: 2011).*
Puangpraphant et al. (2011) Mol. Nutr. Food Res. 55: 1509-1522. (Year: 2011).*
Xing et al. (2012) J. Zhejiang Univ.—Sci. B (Biomed and Biotech) 13(6): 487-493 (Year: 2012).*
Ali, Si, "HPLC-Analysis of Polyphenolic Compounds and Free Radical Scavenging Activity of Pomegranate Fruit (*Punica granatum* L.)." International Journal of Pharmaceutical and Clinical Research, vol. 6. No. 4. 2014.
AMBERLITET™ FPA53 FDA approval letter and Product Data Sheet, DOW, Mar. 5, 2012

(Continued)

*Primary Examiner* — Russell G Fiebig

(57) ABSTRACT

Methods are described herein for making a composition comprising at least one of caffeic acid, monocaffeoylquinic acids, and dicaffeoylquinic acids, and salts thereof.

25 Claims, 10 Drawing Sheets

(56) References Cited

U.S. PATENT DOCUMENTS

| | | | |
|---|---|---|---|
| 10,420,744 | B2 | 9/2019 | Prasad |
| 10,602,758 | B2 | 3/2020 | Dubois |
| 10,772,340 | B2 | 9/2020 | Hotta |
| 10,798,961 | B2 | 10/2020 | Marcq |
| 10,973,794 | B2 | 4/2021 | Forbes |
| 11,000,497 | B2 | 5/2021 | Prasad |
| 2001/0051195 | A1 | 12/2001 | Miljkovic |
| 2002/0187239 | A1 | 12/2002 | Miljkovic |
| 2003/0003212 | A1 | 1/2003 | Chien |
| 2006/0171938 | A1 | 8/2006 | Stock |
| 2010/0099857 | A1 | 4/2010 | Evans |
| 2011/0123505 | A1 | 5/2011 | Ueda |
| 2012/0295857 | A1* | 11/2012 | Goel ............... A61K 36/48 514/26 |
| 2013/0108718 | A1 | 5/2013 | Chabot |
| 2014/0004215 | A1 | 1/2014 | Brownell |
| 2016/0355456 | A1 | 12/2016 | Toyohara et al. |
| 2017/0055548 | A1 | 3/2017 | Chakraborty |
| 2017/0095433 | A1 | 4/2017 | Carter |
| 2017/0095443 | A1 | 4/2017 | Luo |
| 2018/0103670 | A1 | 4/2018 | Recenti |
| 2018/0168212 | A1 | 6/2018 | Markosyan |
| 2018/0177216 | A1 | 6/2018 | Markosyan |
| 2019/0175499 | A1 | 6/2019 | Zhang |
| 2019/0274985 | A1 | 9/2019 | Hotta |
| 2020/0009208 | A1 | 1/2020 | Hwang |
| 2020/0023021 | A1 | 1/2020 | Lewis |
| 2020/0085778 | A1 | 3/2020 | Yamamoto |
| 2020/0138056 | A1 | 5/2020 | Graz |
| 2020/0138765 | A1 | 5/2020 | Prasad |
| 2020/0154737 | A1 | 5/2020 | Dubois |
| 2020/0196649 | A1 | 6/2020 | Mitchell |
| 2020/0197342 | A1 | 6/2020 | Russo |
| 2020/0237845 | A1 | 7/2020 | Suzuki |
| 2020/0275682 | A1 | 9/2020 | Chakraborty |
| 2020/0305483 | A1 | 10/2020 | Gan |
| 2020/0345049 | A1 | 11/2020 | Galano |
| 2021/0037851 | A1 | 2/2021 | Fraser |
| 2021/0051976 | A1 | 2/2021 | Fraser |
| 2021/0084949 | A1 | 3/2021 | Banavara |
| 2021/0092986 | A1 | 4/2021 | Dubois |
| 2021/0128600 | A1 | 5/2021 | Rauch |
| 2021/0153536 | A1 | 5/2021 | Ozato Naoki |
| 2021/0236450 | A1 | 8/2021 | Guthrie |
| 2021/0260013 | A1 | 8/2021 | Lee |
| 2021/0267243 | A1 | 9/2021 | Peterson |

FOREIGN PATENT DOCUMENTS

| | | |
|---|---|---|
| CN | 1326827 A | 8/2005 |
| CN | 1651398 A | 8/2005 |
| CN | 102381974 A | 3/2012 |
| CN | 103040064 A | 4/2013 |
| CN | 102224933 B | 7/2013 |
| CN | 102924544 B | 4/2015 |
| CN | 107027930 A | 8/2017 |
| CN | 107184482 A | 9/2017 |
| DE | 102014016495 A1 | 5/2016 |
| EP | 0730830 A | 9/1996 |
| EP | 1716757 B1 | 7/2009 |
| EP | 2896301 B1 | 6/2016 |
| EP | 2643007 B1 | 8/2016 |
| EP | 3052074 A1 | 8/2016 |
| EP | 2625962 B1 | 6/2017 |
| EP | 3257507 A1 | 12/2017 |
| EP | 3264919 A1 | 1/2018 |
| EP | 2409696 B1 | 6/2018 |
| EP | 2725007 B1 | 10/2018 |
| EP | 2753188 B1 | 1/2019 |
| EP | 2856883 B1 | 3/2019 |
| EP | 3397072 B1 | 7/2019 |
| EP | 3513663 A1 | 7/2019 |
| EP | 3169166 B1 | 8/2019 |
| EP | 3524062 A2 | 8/2019 |
| EP | 2124647 B2 | 12/2019 |
| EP | 3228195 B1 | 1/2020 |
| EP | 3544445 B1 | 5/2020 |
| JP | 58138347 A | 8/1983 |
| JP | 63173531 A | 7/1988 |
| JP | 04145048 A | 5/1992 |
| JP | 0994080 A | 4/1997 |
| JP | 09266767 A | 10/1997 |
| JP | 2009201473 A | 9/2009 |
| JP | 2011168543 A | 9/2011 |
| JP | 2016069324 A | 5/2016 |
| KR | 20070067199 A | 6/2007 |
| KR | 20110043194 | 4/2011 |
| KR | 101227737 B1 | 1/2013 |
| KR | 101500485 | 3/2015 |
| WO | 1998042209 A1 | 10/1998 |
| WO | 2000030464 | 6/2000 |
| WO | 2002041700 A1 | 5/2002 |
| WO | 2007061795 A1 | 5/2007 |
| WO | 2008147725 A1 | 12/2008 |
| WO | 2011112892 A1 | 9/2011 |
| WO | 2013096420 A1 | 6/2013 |
| WO | 2014060244 A1 | 4/2014 |
| WO | 2014146135 A2 | 9/2014 |
| WO | 2014153000 A1 | 9/2014 |
| WO | 2017196933 A1 | 11/2017 |
| WO | 2020172276 W | 8/2020 |
| WO | 2020202193 W | 10/2020 |
| WO | 2020210161 A1 | 10/2020 |
| WO | 2020237060 A1 | 11/2020 |
| WO | 2021038830 W | 3/2021 |
| WO | 2021038832 W | 3/2021 |
| WO | 2021049864 W | 3/2021 |
| WO | 2021081417 A1 | 4/2021 |
| WO | 2021090989 A1 | 5/2021 |
| WO | 2021091322 A1 | 5/2021 |
| WO | 2021091327 A1 | 5/2021 |
| WO | 2021125070 A1 | 6/2021 |
| WO | 2021132439 W | 7/2021 |

OTHER PUBLICATIONS

Anonymous, "Stevia production process | Cargill no-calories sweeteners | Cargill", Nov. 4, 2020 (Nov. 4, 2020), Retrieved from the Internet: URL: https://www.cargill.com/food-beverage/emea/stevia-based-sweeteners-production-process.

Bartoshuk et al., "Sweet Taste of Water Induced by Artichoke," Dec. 1, 1972, Science, 178 (4064), 988-990.

Cilliers, et al., "Total polyphenols in apples and ciders; correlation with chlorogenic acid," Journal of Food Science, vol. 55, No. 5, 1990, pp. 1458-1459.

Clifford, "Chlorogenic acids and other cinnamates—nature, occurance, and dietary burden," Journal of the Science of Food and Agriculture, 79:362-372 (1999).

Craig et al., "Performance review of a fast HPLC-UV method for the quantification of chorogenic acids in green coffee bean extracts," Talanta, 154 (2016) 481-485.

Cros et al., "Solvent Extraction of Oil and Chlorogenic Acid from Green Cofffee Part I: Equilibrium Data," Journal of Food Engineering 10 (1989) 1-11.

DIAION WA10, Mitsubishi Chemical, commercial product available since at least 1998.

Edgar Naegele, "Determination of Chlorogenic Acid in Coffee Products According to DIN 10767," Sep. 1, 2016, Agilent Technology, INC.

Fu et al., "Production of chlorogenic acid and its derivatives in hairy root cultures of Stevia rebaudiana," Jan. 14, 2015, Journal of Agricalatural and Food Chemistry, 63(1):262-268.

Gawel-Beben et al., "*Stevia rebuadiana* Bert. Leaf extracts as a multifunctional source of natural antioxidants," Molecules, Mar. 27, 2015.

Hernandez T et al., "Variations in the phenolic composition of fruit juices with different treatments," European Food Research and Technology, vol. 204, No. 2, 1997, p. 151-155.

(56) References Cited

OTHER PUBLICATIONS

Kellie P Burris et al, "Composition and Bioactive Properties of Yerba Mate (*Ilex paraguariensis* A. St-Hil.): A Review", Chillán Jun. 2012 (Jun. 2012), p. 268-275.

Kremr et al., "Unremitting Problems with Chlorogenic Acid Nomenclature: A Review," Quim. Nova, vol. 39, No. 4, 530-533, 2016.

Ky et al., "Camparison of Five Purification Methods for Chlorogenic Acids in Green Coffee Beans (*Coffee* sp.)," J. Agric. Food Chem. 1997, 45, 786-790, obtained from https://horizon.documentation.ird.fr/exl-doc/pleins_textes/pleins_textes_6/b_fdi_47-48/010010457.pdf.

Lee et al., "Chicoric acid: chemistry distribution, and production," Frontiers in Chemistry, 2013, 1(40).

Maietta et al., "Artichoke (*Cynara cardunculus* L. var. scolymus) waste as a natural source of carbonyl trapping and antiglycative agents," Food Research International, 100 (2017) 780-790.

Meinhart et al., "Analysis of chlorogenic acids isomers and caffeic acid in 89 herbal infusions (tea)," Journal of Food Composition and Analysis, 73 (2018) 76-82.

Meinhart et al., "Chlorogenic acid isomer contents in 100 plants commercialized in Brazil," Food Research International, 99 (2017) 522-530.

Meireles et al., "Stevia (*Stevia rebaudiana* Bertoni):—Futuristic view of the sweeter side of life," Floriculture, Ornamental and Plant Biotechnology Volumn IV, 2006, Global Science Books.

Moller et al., "Analysis of Quinic Acid Esters of Hydroxycinnamic acids in Plant Material by Capillary Gas Chromatography and High-Performance Liquid Chromatography," Journal of Chromatography, 241(1982) 371-379.

Ohta et al., "Characterization of Novel Steviol Glycosides from Leaves of Stevia rebaudiana Morita," 2010, J. Appl. Glycosci., 57, 199-209.

Relite RAM2, Resindion Resins for Food Treatments, 2016.

Rogers et al., "Changes to the content of sugars, sugar alcohols, myo-inositol, carboxylic acids and inorganic anions in developing grains from different varieties of Robusta (*Coffee canephora*) and Arabica (*C. arabica*) coffees," Plant Science, 1999, 149, 115-123.

Schmidt J. M. et al., "A New Two-Step Chromatographic Procedure for Fractionation of Potato Proteins with Potato Fruit Juice and Spray-Dried Protein as Source Materials", Food and Bioprocess Technology, An International Journal, Springer-Berlag, New York, vol. 10, No. 11, Jul. 26, 2017, pp. 1946-1958, XP036329673, ISSN: 1935-5130, DOI:10.1007/S11947-017-1966-4.

Sepabeads SP70, Mitsubishi Chemical, commercial product available since at least 2002.

Shibata et al., "Glucosylation of steviol and steviol-glucosides in extracts from Stevia rebaudiana Bertoni," Plant Physiol., 1991, 95, 152-156.

Standard Method Performance Requirements (SMPRs) for Determination of Phenolic Compounds in Dietary Supplements and Dietary Ingredients Containing Echinacea, Sep. 22, 2017, AOAC International.

Suarez-Quiroz et al., "Isolation of green coffee chlorogenic acids using activated carbon," Journal of Food Composition and Analysis, 2014, 33:55-58.

Trugo et al., Chlorogenic Acid Composition of Instant Coffees, Analyst, Mar. 1984, vol. 109, pp. 263-266.

Weidel et al., "A Rapid Method for Quantifying Chlorogenic Acid Levels in Potato Samples," Journal of AOAC International, vol. 97, No. 3, Nov. 3, 2014.

Wildermuth et al., "Chlorogenic acid oxidation and its reaction with sunflower proteins to form green-colored complexes," Comprehensive Reviews in Food Science and Food Safety, 2016, vol. 15, 829-843.

Marques V. X. and Farah A. (2010) Urinary excretion of chlorogenic acids and metabolites in humans after green mate (*I. paraguariensis*) consumption. FASEB J. 24, 1, Suppl., [abstract 922.1]. DOI:10.1096/fasebj.24.1_supplement.922.1.

Matsumoto R. L. T., et al. (2009) Effects of maté tea (*Ilex paraguariensis*) ingestion on mRNA expression of antioxidant enzymes, lipid peroxidation, and total antioxidant status in healthy young women. J. Agric. Food Chem. 57, 1775-1780. DOI:10.1021/jf803096g.

Mello F. W., et al. (2018) Maté consumption association with upper aerodigestive tract cancers: a systematic review and meta-analysis. Oral Oncol. 82, 37-47 [plus supplementary data]. DOI:10.1016/koraloncology.2018.04.023.

Messina D., et al. (2017) Maté tea and lipid profile in overweight women under caloric restriction. Ann Nutr. Metab. 71, 384 [abstract 144-1131]. DOI:101159/000480486.

Mikulasova M., et al. (2005) Genotoxic effects of the hydroxycinnamic acid derivatives—caffeic, chlorogenic and cichoric acids. Biologia (Bratisl.) 60, 275-279.

Minuzzi Becker A., et al. (2019) Spray-dried yerba mate extract capsules: clinical evaluation and antioxidant potential in healthy individuals. Plant oods Hum. Nutr. 74, 495-500 [plus supplementary tables]. DOI:10.1007/s11130-019-00764-4.

Miranda D. D. C., et al. (2008) Protective effects of mate tea (*Ilex paraguariensis*) on H2O2-induced DNA damage and DNA repair in mice. Mutagenesis 23, 261-265. DOI:10.1093/mutage/gen011.

Monteiro M., et al. (2007) Chlorogenic acid compounds from coffee are differentially absorbed and metabolized in hiumans. J. Nutr. 137, 2196-2201. DOI:10.1093/jn/137.10.2196.

Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.

Nakamura S., et al. (2006) [Pharmacokinetics of chlorogenic acids absorbed in human plasma and their metabolites following oral ingestion of coffee drink]. Yakuri To Chiryo [Jpn. Pharmacol. Ther.] 34, 1239-1246.

Naylor L. H., et al. (2021) Acute dose-response effect of coffee-derived chlorogenic acids on the human vasculature in healthy volunteers: a randomized controlled trial. Am. J. Clin. Nutr. 113, 370-379. D01:10.1093/ajcninqaa312.

Nowacki L. C., et al. (2021) Ilex paraguariensis extract as an alternative to pain medications. Acta Pharm. 71, 383-398. DOI:10.2478/acph-2021-0029.

Ochiai R., et al. (2019) Effect of chlorogenic acids on cognitive function in mild cognitive impairment: a randomized controlled crossover trial. J. Alzheimers Dis. 72, 1209-1216 [plus supplementary tables]. DOI:10.3233/jad-190757.

Olthof M. R., et al. (2001a) Consumption of high doses of chlorogenic acid, present in coffee, or of black tea increases plasma total homocysteine concentrations in humans. Am. J. Clin. Nutr. 73, 532-538. DOI:10.1093/ajcn/73.3.532.

Olthof M. R., et al. (2001b) Chlorogenic acid and caffeic acid are absorbed in humans. J. Nutr. 131, 66-7t DOI:10.1093/jn/131.1.66.

Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.

Onakpoya I. J., et al. (2015) the effect of chlorogenic acid on blood pressure: a systematic review and meta-analysis of randomized clinical trials. J. Hum. Hypertens. 29, 77-81 [plus supplementary data]. DOI:10.1038/ ihh.2014A6.

Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.

Pereira Panza V., et al. (2019) Effect of mate tea (*Ilex paraguariensis*) on the expression of the leukocyte NADPH pxidase subunit p47phox and on circulating inflammatory cytokines in healthy men: a pilot study. Int. J. Food Sci. Nutr. 70, 212-221D01:10.1080/09637486.2018.1486393.

Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390::AID-JSFA258>3.0.CO;2-0.

Renouf M., et al. (2014) Dose-response plasma appearance of coffee chlorogenic and phenolic acids in adults. Mol. Nutr. Food Res. 58, 301-309. DOI:10.1002/mnfr.201300349.

(56) References Cited

OTHER PUBLICATIONS

Richling E., et al. (2012) Dose-response relationship of chlorogenic acids in humans. Naunyn Schmiedebergs ArchPharmacol. 385, S75 [abstract 327]. DOI:10.1007/s00210-012-0736-0.

Rocha D. S., et al. (2018) Effect of yerba mate (*Ilex paraguariensis*) extract on the metabolism of diabetic rats. Biomed. Pharmacother. 105, 370-376 [plus supplementary figure]DOI:10.1016/j.biopha.2018.05.132.

Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/jmf.2018.0060.

Sanchez Boado L., et al (2018) Effects of Ilex paraguariensis polyphenols on magnesium absortion and iron bioavailability: preliminary study. J. Food Res. 7, 114-126. DOI:10.5539/jfr.v7n2p114.

Sarria B., et al. (2020a) Yerba mate may prevent diabetes according to a crossover, randomized, controlled study in humans. Proc. Nutr. Soc. 79, OCE2, E245 DOI:10.1017/30029665120001937.

Sarria B., et al. (2020b) Yerba mate improves cardiovascular health in normocholesterolemic and hypercholesterolemic subjects. Proc. Nutr. Soc. 79, OCE2, E635. DOI: 10.1017/S0029665120005844.

Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.

Simao Do Carmo L., et al. (2013) the effects of yerba maté (*Ilex paraguariensis*) consumption on IL-1, IL-6, TNF-α and IL-10 production by bone marrow cells in Wistar rats fed a high-fat diet. Int J Vitam Nutr Res 83, 26-35. DOI:10.1024/0300-9831/a000142.

Sirima Puangpraphant et al: "Dicaffeoylquinic acids in Verba mate (*Ilex paraguariensis* St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, 8 Oct. 2011 (Oct. 8, 2011), pp. 1509-1522, XP055175515, ISSN: 1613-4125, DOI: 10.1002/mnfr201100128.

Song Z., et al. (2014) [Effect of chlorogenic acid at high dose on expression of hepatic inflammatory cytokines mRNA induced by lipopolysaccharides]. Ying Yang Xue Bao [Acta Nutr. Sin.] 36, 481-485.

Souza S. J., et al. (2017) Effect of chocolate and mate tea on the lipid profile of individuals with HIV/AIDS on antiretroviral therapy: a clinical trial. Nutrition 43-44, 61-68. DOI:10.1016/j.nut.2017.06.017.

Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.

Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.

Stich H. F., et al. (1981) A comparative genotoxicity study of chlorogenic acid (3-O-caffeoylquinic acid). Mutat. Res. 90, 201-212. DOI:10.1016/0165-1218(81)90001-X.

Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.

U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.

U.S. FDA (2018) Part 182—Substances generally recognized as safe. Section §182.20—Essential oils, oleoresins (solvent-free), and natural extractives (including distillates). In: U.S. Code of Federal Regulations (CFR). Title 21: Food and Drugs. (U.S. Food and Drug Administration). U.S. Government Printing Office (GPO), Washington, DC.

Vargas Alves R. J., et al. (2008) The evaluation of maté (*Ilex paraguariensis*) genetic toxicity in human lymphocytes by the cytokinesis-block in the micronucleus assay. Toxicol. In Vitro 22, 695-698. DOI:10.1016/j.tiv.2007.11.005.

Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.

Wantanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.

Wei Z.-M., et al. (2010) [Clinical tolerability of 1,5-dicaffeoylquinic acid tablets]. Zhongguo Xin Yao Za Zhi [Chin. J. New Drugs] 19, 106-108.

Wnuk M., et al. (2009) Evaluation of the cyto- and genotoxic activity of yerba mate (*Ilex paraguariensis*) in human lymphocytes in vitro. Mutat. Res. 679, 18-23. DOI:10.1016/j.mrgentox.2009.07.017.

Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.

Yara Queiroz et al: The Chlorogenic Acid and Caffeine Content of Verba Mate (*Ilex paraguariensis*) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821.pdf [retrieved on Jul. 15, 2020].

Yu S., et al. (2015) Yerba mate (*Ilex paraguariensis*) improves microcirculation of volunteers with high blood viscosity: a randomized, double-blind, placebo-controlled trial. Exp. Gerontol. 62, 14-22 [plus supplementary tables]. DOI:10.1016/texger.2014.12.016.

Zhu Y., et al. (2017) [Effect of caffeine and chlorogenic acid on body weight, lipid accumulation and the expression of lipid metabolism-related genes in high-fat diet-fed mice]. Shipin Kexue [Food Sci.] 38, 162-167 DOI:10.7506/spkx1002-6630-201709026.

Zuniga L. Y. et al.(2018) Effect of chlorogenic acid administration on glycemic control, insulin secretion, and insulin sensitivity in patients with impaired glucose tolerance. J. Med. Food 21, 469-473. DOI:10.1089/jmf.2017.0110.

Abeywardena M. Y., et al. (2010) Acute administration of chlorogenic acid reduces blood pressure in the rat. Hypertension 55, 1493 [abstract 002]. DOI:10.1161/HYP.0b013e3181df4279.

Albas C. S., et al (2014) Avaliação da genotoxicidade da *Ilex paraguariensis* (erva mate) pelo teste do micronúcleo / [Evaluation of the genotoxicity of *Ilex paraguariensis* (yerba mate) by micronucleus test]. Rev. Bras. Plantas Med. 16, 2, Suppl 1, 345-349 [Portuguese, English abstract]. DOI:10.1590/1983-084X/12_058.

Alkhatib A. and Atcheson, R. (2017) Yerba maté (*ilex paraguariensis*) metabolic, satiety, and mood state effects at rest and during prolonged exercise. Nutrients 9, 882 [15pp]. DOI:10.3390/nu9080882.

Baeza Gema et al: "Dihydrocaffeic acid, a major microbial metabolite of chlorogenic acids, shows similar protective affect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI:10.1016/J.FOODRES.2016.06.011.

Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI:10.1186/s12937-018-0426-y.

Bariana D. S., et al. (1965) Chlorogenic acid: further evidence for its antigenic and allergenic activity. Nature 207, 1155-1157. DOI:10.1038/2071155a0.

Bidau C. J., et al. (2004) Evaluation of the genotoxicity of aqueous extracts of Ilex paraguariensis St. Hil. (Aquifoliaceae) using the Allium test. Cytologia 69, 109-117. DOI:10.1508/cytologia.69.109.

Boaventura B. C., et al (2012) Association of mate tea (*Ilex paraguariensis*) intake and dietary intervention and effects on oxidative stress biomarkers of dyslipidemic subjects. Nutrition 28, 657-664. DOI:10.1016/j.nut.2011.10.017.

(56) References Cited

OTHER PUBLICATIONS

Boaventura B. C., et al (2013) Antioxidant potential of mate tea (*Ilex paraguariensis*) in type 2 diabetic mellitus and pre-diiabetic individuals. J. Funct. Foods 5, 1057-1064. DOI:10.1016/jp.2013.03.001.

Boaventura B. C., et al (2015) Effect of yerba mate (*Ilex paraguariensis* A. St. Hil.) infusion obtained by freeze concentration technology on antioxidant status of healthy individuals. LWT Food Sci. Technol. 62, 948-954. DOI:10.1016/j.lwt.2015.02.028.

Boaventura, B. C. B., et al (2013). Enhancement of bioactive compounds content and antioxidant activity of aqueous extract of mate (*Ilex paraguariensis* A. St. Hil.) through freeze concentration technology. Food Research International, 53, 686e692.

Borges M. C., et al. (2013) the effect of mate tea (*Ilex paraguariensis*) on metabolic and inflammatory parameters in high-fat diet-fed Wistar rats. Int. J. Food Sci. Nutr. 64, 561-569. DOI:10.3109/09637486.2012.759188.

Bortoluzzi M.-C., et al (2014) Frequency of micronucleus in oral epithelial cells after exposure to mate-tea in healthy humans. Med. Oral Patol. Oral Cir. Bucal. 19, e345-e349. DOI:10.4317/medoral.19570.

Carvalho Ribeiro M., et al (2017) the effects of roasted yerba mate (*Ilex paraguariensis* A, ST. Hil.) consumption on glycemia and total serum creatine phosphokinase in patients with traumatic brain injury. J. Funct. Foods 28, 240-245. DOI:10.1016/j.jff.2016.11.

Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.

Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.

Cuesta A., et al (2018) Efecto agudo del consumo de yerba mate (*Ilex paraguariensis*) sobre el ritmo cardíaco en pacientes derivados para estudio Holter [Acute effect of yerba mate (*Ilex paraguariensis*) consumption on heart rhythm in patients referred for Holter study] [epub ahead of print]. Arch. Cardiol. Mex. xxx, Jun. 2, 2018 [1-6] [Spanish, English abstract]. DOI:10.1016/j.acmx.2018.05.004.

de Andrade F., Coehlo de Albuquerque C. A., Maraschin M. and da Silva E. L. (2012) Safety assessment of yerba mate (*Ilex paraguariensis*) dried extract: results of acute and 90 days subchronic toxicity studies in rats and rabbits. Food Chem. Toxicol. 50, 328-334. DOI:10.1016/.fct.2011.08.028.

De Meneses Fujii et al. (2014) Yerba Mate (*Ilex paraguariensis*) modulates NF-kappaB pathway and AKT expression in the liver of rats fed on a high-fat diet. Int. J. Food Sci. Nutr. 65, 967-976. DOI:10.3109/09637486.2014.945153.

de Morais E. C., et al. (2009) Consumption of yerba mate (*Ilex paraguariensis*) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.

Eklund A. (1975) Effect of chlorogenic acid in a casein diet for rats. Nutritional and pathological observations. Nutr. Metab. 18, 258-264. DOI:101159/000175603.

Enokuchi Y., et al. (2020) Effects of chlorogenic acids on menopausal symptoms in healthy women: a randomized, placebo-controlled, double-blind, parallel-group trial. Nutrients 12, 3757 [12pp]. DOI:10.3390/nu12123757.

Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.

Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.

Fonseca C. A., et al (2000) Nontoxic, mutagenic, and clastogenic activities of mate-chimarrao (*Ilex paraguariensis*). J. Environ. Pathol. Toxicol. Oncol. 19, 333-346.

Frank J., et al. (2003) the dietary hydroxycinnamate caffeic acid and its conjugate chlorogenic acid increase vitamin E and cholesterol concentrations in Sprague-Dawley rats. J. Agric. Food Chem. 51, 2526-2531. DOI:10.1021/if026127k.

Freedman S. O., et al. (1961) Chlorogenic acid: an allergen in green coffee bean. Nature 192, 241-243. DOI:10.1038/192241a0.

Freedman S. O., et al. (1964) Antigenic and allergenic properties of chlorogenic acid man, rabbit, guinea pig. Can. Med. Assoc. J. 90, 473-474.

Gebara K. S., et al. (2020) a randomized crossover intervention study on the effect a standardized maté extract (*Ilex paraguariensis* A. St.-Hil.) in Men predisposed to cardiovascular risk. Nutrients, 13, 14 [14pp]. DOI:10.3390/nu13010014.

Gómez-Juaristi M., Martinez-López S., Sarria B., Bravo L. and Mateos R. (2018) Absorption and metabolism of yerba mate phenolic compounds in humans. Food Chem. 240, 1028-1038. DOI:10.1016/j.foodchem.2017.08.003.

Gonthier M.-P., et al. (2006) Microbial metabolism of caffeic acid and its esters chlorogenic and caftaric acids by human faecal microbiota in vitro. Biomed. Pharmacother. 60, 536-540. D01:10.1016/j.biopha.2006.07.084.

Grzesiuk J. D., et al (2012) Evaluation of mutagenicity and antimutagenicity of *Ilex paraguariensi*} A. St.-Hil.: Aquifoliaceae infusion on Allium cepa assay. Arq. Cienc. Saude UNIPAR 16, 73-78. DOI:10.25110/arqsaude.v16i2.2012.4840.

Gu R., et al. (2007) Simultaneous determination of 1,5-dicaffeoylquinic acid and its active metabolites in human plasma by liquid chromatography—tandem mass spectrometry for pharmacokinetic studies. J. Chromatogr. B. 852, 85-91. DOI:10.1016/j.jchromb.2006.12.055.

Hernandes L. C., et al. (2016) Cytotoxicity and genotoxicity of chlorogenic acid alone or associated with the Demethylating drug 5-azacytidine in Jurkat cells. Toxicol. Lett. 258, Suppl. S, S56 [abstract OSC01-007]. DOI:10.1016/i.toxlet.2016.06.1295.

IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).

IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496. Lyon, France: International Agency for Research on Cancer (IARC), Lyon, France.

International Search Report and Written Opinion dated Sep. 10, 2020 to International Application No. PCT/US2020/026885 (15 pages).

Jin S., et al.(2015) Chlorogenic acid improves late diabetes through adiponectin receptor signaling pathways in db/db mice. PLoS One 10, e0120842 [15pp]. DOI:10.1371/journal.pone.0120842.

Kato M., et al. (2018) Effect of chlorogenic acid intake on cognitive function in the elderly: a pilot study. Evid. Based. Complement. Alternat. Med. 2018, Article ID 8608497 [8pp]. DOI:10.1155/2018/8608497.

Kim H. J., et al. (2012) Effect of green mate in overweight volunteers: a randomised placebo-controlled human study. J. Funct. Foods 4, 287-293. DOI:10.1016/j.jff.2011.12.005.

Kim S.-Y., et al. (2015) Anti-obesity effects of Yerba Mate (*Ilex paraguariensis*): a randomized, double-blind, placebo-controlled clinical trial. BMC Complement. Altern. Med. 15, 338 [8pp]. DOI:10.1186/s12906-015-0859-1.

Klein G. A. et al (2011) Mate tea (*Ilex paraguariensis*) improves glycemic and lipid profiles of type 2 diabetes and pre-diabetes individuals: a pilot study. J. Am. Coll. Nutr. 30, 320-332.

Kujawska M (2018) Yerba mate (*Ilex paraguariensis*) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.

(56) References Cited

OTHER PUBLICATIONS

Laird Layton L., et al. (1964) Pure chlorogenic acid is not allergenic in atopy to green coffee: A specific protein probably is involved. Nature 203, 188-189. DOI:10.1038/203188a0.

Leitão A. C. and Braga R. S. (1994) Mutagenic and genotoxic effects of mate (*Ilex paraguariensis*) in prokaryotic organisms. Braz. J. Med. Biol. Res. 27, 1517-1525.

Lin M., et al.(2013) Evaluation of the potential sensitization of chlorogenic Acid: a meta-analysis. Evid. Based. Complement. Alternat. Med. 2013, Article Id 208467 DOI:10.1155/2013/208467.

Liu B., et al.(2017) Preparation, phytochemical investigation, and safety evaluation of chlorogenic acid products from Eupatonum adenophorum. Molecules 22, 67 [12pp]. DOI:10.3390/molecules22010067.

Liu Z., et al. (2010) Evaluation of the immunosensitizing potential of chlorogenic acid using a popliteal lymph node assay in BALB/c mice. Food Chem. Toxicol. 48, 1059-1065. DOI:10.1016/j.fct.2010.01.024.

Lorena Deladino et al: "Major Phenolics in Verba Mate Extracts (*Ilex paraguariensis*) and Their Contribution to the Total Antioxidant Capacity", Food and Nutrition Sciences, vol. 04, Aug. 1, 2013 (Aug. 1, 2013), pages 154-162, XP055588480, ISSN: 2157-944X, DOI: 10.4236/fns.2013.48A019.

Lowell F. C. (1965) Allergenicity of chlorogenic acid. J. Allergy 36, 308. DOI:10.1016/0021-8707(65)90091-2.

\* cited by examiner

| Peak Name | Ret.Time Min | Rel.Area % | Peak Name | Ret.Time min | Rel.Area % | Peak Name | Ret.Time min | Rel.Area % |
|---|---|---|---|---|---|---|---|---|
| | 2.149 | 0.08 | | 7.508 | 0.06 | Cynarin isomer 3 | 11.761 | 0.08 |
| | 2.39 | 1.83 | | 7.575 | 0.08 | | 11.813 | 0.31 |
| | 2.645 | 0.1 | | 7.664 | 0.18 | 3,4-DCQA | 11.965 | 7.53 |
| Neochlorogenic acid | 2.751 | 10.89 | | 7.755 | 0.16 | | 12.195 | 0.13 |
| | 2.855 | 0.31 | | 7.905 | 0.05 | | 12.29 | 0.09 |
| | 2.91 | 0.35 | | 7.96 | 0.13 | | 12.367 | 0.15 |
| | 3.02 | 0.17 | | 8.008 | 0.08 | | 12.493 | 0.08 |
| | 3.145 | 0.35 | | 8.105 | 0.33 | | 12.57 | 0.05 |
| | 3.394 | 2.47 | | 8.2 | 0.08 | | 12.644 | 0.15 |
| | 3.635 | 0.85 | | 8.309 | 0.2 | | 12.695 | 0.08 |
| | 3.767 | 0.43 | | 8.397 | 0.16 | | 12.86 | 0.08 |
| | 3.903 | 0.22 | | 8.491 | 0.1 | | 13.087 | 0.03 |
| | 3.943 | 0.26 | | 8.6 | 1.49 | | 13.19 | 0.02 |
| | 4.032 | 0.25 | | 8.665 | 0.14 | | 13.542 | 0.23 |
| | 4.173 | 0.37 | | 8.746 | 0.08 | | 13.656 | 0.01 |
| | 4.29 | 0.34 | | 8.852 | 0.27 | | 13.732 | 0.15 |
| | 4.399 | 0.12 | | 8.937 | 0.12 | | 13.811 | 0 |
| Chlorogenic acid | 4.544 | 8.88 | | 9.021 | 0.08 | | 13.909 | 0.08 |
| Caffeic Acid | 4.693 | 0.42 | | 9.097 | 0.22 | | 13.99 | 0.09 |
| Cryptochlorogenic acid | 4.759 | 5.69 | | 9.209 | 0.25 | | 14.245 | 0.04 |
| | 4.952 | 0.22 | Rutin (or isomer) | 9.34 | 5.04 | | 14.377 | 0.08 |
| | 5.043 | 0.12 | | 9.55 | 0.88 | | 14.427 | 0.31 |
| | 5.169 | 0.18 | | 9.6 | 0.26 | | 14.64 | 0.02 |
| | 5.257 | 0.38 | | 9.675 | 0.1 | | 14.75 | 0.08 |
| | 5.335 | 0.08 | | 9.79 | 0.22 | | 14.892 | 0.02 |
| | 5.429 | 0.03 | | 9.865 | 0.03 | | 14.982 | 0.04 |
| | 5.551 | 0.12 | | 9.92 | 0.07 | | 15.145 | 0.02 |
| Caffeine | 5.671 | 18.53 | | 10.052 | 0.04 | | 15.55 | 0.05 |
| | 5.796 | 5.49 | | 10.162 | 0.04 | | 16.1 | 0.17 |
| | 6.051 | 0.1 | | 10.205 | 0.03 | | 16.692 | 0.02 |
| | 6.128 | 0.05 | | 10.287 | 0.06 | | 16.953 | 0.04 |
| | 6.175 | 0.04 | | 10.326 | 0.03 | | 18.76 | 0.06 |
| | 6.242 | 0.09 | | 10.455 | 0.11 | | 18.822 | 0.05 |
| | 6.314 | 0.03 | Cynarin isomer 1 | 10.562 | 2.55 | | 18.935 | 0.02 |
| | 6.49 | 0.19 | | 10.664 | 0.08 | | 19.027 | 0.02 |
| | 6.691 | 0.07 | Cynarin | 10.792 | 0.92 | | 19.363 | 0.15 |
| | 6.77 | 0.02 | 3,5-DCQA | 10.902 | 12.66 | | 19.483 | 0.02 |
| | 6.971 | 0.04 | | 11.025 | 0.38 | | 20.013 | 0.02 |
| | 7.05 | 0.05 | Cynarin isomer 2 | 11.212 | 0.05 | | 20.082 | 0.02 |
| | 7.143 | 0.03 | | 11.275 | 0.13 | | 20.216 | 0.04 |
| | 7.23 | 0.03 | | 11.336 | 0.07 | | 20.267 | 0.06 |
| | 7.289 | 0.13 | | 11.413 | 0.17 | | 20.506 | 0.03 |
| | 7.36 | 0.02 | | 11.505 | 0.02 | | 20.68 | 0.3 |
| | 7.45 | 0.18 | | 11.585 | 0.04 | | 20.779 | 0.15 |
| | | | | | | | 20.985 | 0 |

FIG. 8

| Peak Name | Ret.Time | Rel.Area | Peak Name | Ret.Time | Rel.Area |
|---|---|---|---|---|---|
| | min | % | | min | % |
| | 2.145 | 0.11 | | 8.111 | 0.15 |
| | 2.218 | 0.03 | | 8.206 | 0.1 |
| | 2.276 | 0.05 | | 8.271 | 0 |
| | 2.636 | 0.14 | | 8.325 | 0.22 |
| Neochlorogenic acid | 2.749 | 19.29 | | 8.407 | 0.12 |
| | 3.011 | 0.18 | | 8.497 | 0.08 |
| | 3.121 | 0.23 | | 8.558 | 0.16 |
| | 3.33 | 0.03 | | 8.61 | 0.47 |
| | 3.396 | 0.33 | | 8.681 | 0.15 |
| | 3.685 | 0.34 | | 8.762 | 0.13 |
| | 3.738 | 0.42 | | 8.872 | 0.3 |
| | 3.952 | 0.35 | | 8.944 | 0.14 |
| | 4.039 | 0.26 | | 9.08 | 0.3 |
| | 4.173 | 0.3 | | 9.215 | 0.21 |
| | 4.306 | 0.07 | Rutin (or isomer) | 9.356 | 0.16 |
| | 4.412 | 0.1 | | 9.474 | 0.03 |
| | 4.461 | 0.04 | | 9.551 | 0.12 |
| Chlorogenic acid | 4.548 | 16.09 | | 9.639 | 0.22 |
| Caffeic Acid | 4.7 | 0.63 | | 9.734 | 0.01 |
| Cryptochlorogenic acid | 4.763 | 11.59 | | 9.841 | 0.04 |
| | 4.957 | 0.22 | | 9.942 | 0.07 |
| | 5.05 | 0.09 | | 10.1 | 0.03 |
| | 5.113 | 0.06 | | 10.219 | 0.05 |
| | 5.173 | 0.06 | | 10.343 | 0.04 |
| | 5.261 | 0.46 | | 10.41 | 0.03 |
| | 5.343 | 0.05 | | 10.432 | 0.03 |
| | 5.531 | 0.03 | Cynarin isomer 1 | 10.573 | 5 |
| Caffeine | 5.683 | 0.11 | Cynarin | 10.675 | 0.08 |
| | 5.806 | 1.23 | 3,5-DCQA | 10.914 | 19.59 |
| | 5.946 | 0.03 | Cynarin isomer 2 | 11.171 | 0.09 |
| | 6.051 | 0.06 | | 11.289 | 0.13 |
| | 6.185 | 0 | | 11.346 | 0.09 |
| | 6.249 | 0.17 | | 11.486 | 0.07 |
| | 6.337 | 0.02 | | 11.601 | 0.05 |
| | 6.517 | 0.06 | Cynarin isomer 3 | 11.722 | 0.03 |
| | 6.707 | 0.04 | | 11.776 | 0.08 |
| | 7.003 | 0.05 | | 11.828 | 0.09 |
| | 7.066 | 0.03 | 3,4-DCQA | 11.975 | 14.68 |
| | 7.156 | 0.03 | | 12.357 | 0.11 |
| | 7.294 | 0.1 | | 12.506 | 0.11 |
| | 7.403 | 0.03 | | 12.657 | 0.28 |
| | 7.462 | 0.29 | | 12.875 | 0.12 |
| | 7.522 | 0.11 | | 13.204 | 0.03 |
| | 7.581 | 0.12 | | 13.55 | 0.31 |
| | 7.671 | 0.21 | | 13.74 | 0.17 |
| | 7.721 | 0.11 | | 13.997 | 0.07 |
| | 7.751 | 0.11 | | 14.386 | 0.05 |
| | 7.913 | 0.01 | | 14.437 | 0.32 |
| | 7.966 | 0.13 | | 14.761 | 0.1 |
| | 8.014 | 0.16 | | 16.109 | 0.27 |

FIG. 9

| Peak Name | Ret.Time min | Rel.Area % | Peak Name | Ret.Time min | Rel.Area % |
|---|---|---|---|---|---|
| | 2.154 | 0.07 | | 7.244 | 0.05 |
| | 2.636 | 0.25 | | 7.467 | 0.47 |
| Neochlorogenic acid | 2.764 | 15.85 | | 7.612 | 0 |
| | 3.024 | 0.13 | | 7.675 | 0.26 |
| | 3.163 | 0.2 | | 7.73 | 0.12 |
| | 3.412 | 0.18 | | 8.617 | 0.22 |
| | 3.462 | 0.07 | Rutin (or isomer) | 9.351 | 0.13 |
| | 3.691 | 0.1 | | 9.553 | 0.1 |
| | 3.764 | 0.09 | | 9.64 | 0.06 |
| | 3.97 | 0.13 | | 10.203 | 0.08 |
| | 4.055 | 0.16 | Cynarin isomer 1 | 10.565 | 6.1 |
| | 4.196 | 0.07 | Cynarin | 10.684 | 0.1 |
| Chlorogenic acid | 4.564 | 20.7 | 3,5-DCQA | 10.907 | 18.99 |
| Caffeic Acid | 4.714 | 0.41 | Cynarin isomer 2 | 11.205 | 0.05 |
| Cryptochlorogenic acid | 4.781 | 14.76 | | 11.279 | 0.13 |
| | 4.983 | 0.06 | | 11.337 | 0.11 |
| | 5.281 | 0.54 | 3,4-DCQA | 11.969 | 16.22 |
| | 5.364 | 0.05 | | 12.351 | 0.12 |
| | 5.549 | 0.06 | | 12.403 | 0.13 |
| Caffeine | 5.699 | 0.27 | | 12.649 | 0.3 |
| | 5.823 | 0.71 | | 12.863 | 0.1 |
| | 5.889 | 0.1 | | 13.545 | 0.23 |
| | 6.066 | 0.06 | | 13.735 | 0.11 |
| | 6.261 | 0.19 | | 13.998 | 0.11 |
| | 6.528 | 0.05 | | 14.459 | 0.3 |
| | 6.713 | 0.05 | | 14.774 | 0.08 |

FIG. 10

METHODS FOR MAKING YERBA MATE EXTRACT COMPOSITION

CROSS-REFERENCE TO RELATED APPLICATIONS

This application is a Continuation of International Application No. PCT/US2018/054688, filed Oct. 5, 2018, entitled "Methods for Making Yerba Mate Extract Composition", which claims the benefit of U.S. Provisional Application No. 62/569,279, filed Oct. 6, 2017, and entitled "Steviol Glycoside Solubility Enhancers," and U.S. Provisional Application No. 62/676,722, filed May 25, 2018, and entitled "Methods for Making Yerba Mate Extract Composition", each of which is hereby incorporated by reference in its entirety.

BACKGROUND

Yerba mate is a species of the holly genus (*Ilex*), with the botanical name *Ilex paraguariensis*. Yerba mate is sometimes used to make the beverage known as "mate," traditionally consumed in central and southern regions of South America, primarily in Paraguay, as well as in Argentina, Uruguay, southern and central-western Brazil, the Chaco region of Bolivia and southern Chile. Yerba mate can also be found in various energy drinks on the market today.

Yerba mate has been claimed to have various effects on human health and these effects have been attributed to the high quantity of polyphenols found in mate tea. For example, yerba mate may improve allergy symptoms; reduce the risk of diabetes mellitus; and may reduce high blood sugar, at least in mice. In addition, mate also contains compounds that can act as an appetite suppressant; act to increase mental energy and focus; can improve mood; and can promote deeper sleep. Finally, yerba mate consumption has been linked to benefits, including in reduction of fat cells, inflammation, cholesterol, lipids.

SUMMARY

Because of the various salutary effects of yerba mate, there is an interest in methods for extracting various compounds believed to be responsible for those effects, from yerba mate biomass. These compounds include, but are not limited to, caffeic acid, monocaffeoylquinic acids (e.g., chlorogenic acid, neochlorogenic acid, and cyrptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

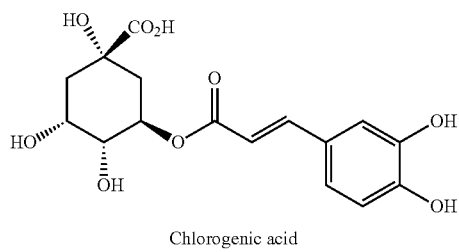

Chlorogenic acid

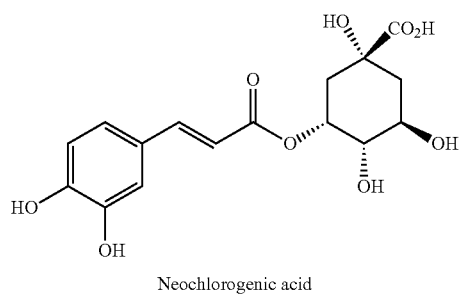

Neochlorogenic acid

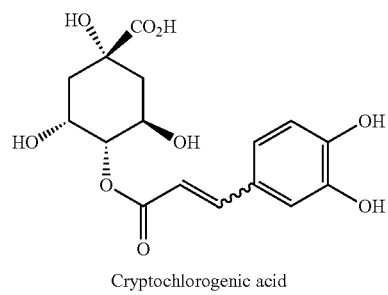

Cryptochlorogenic acid

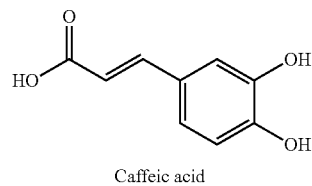

Caffeic acid

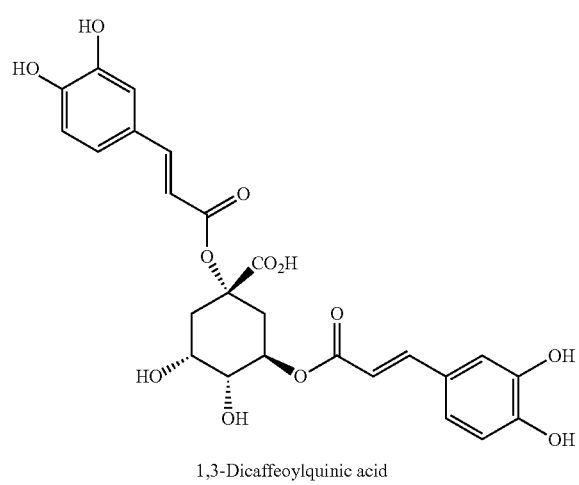

1,3-Dicaffeoylquinic acid

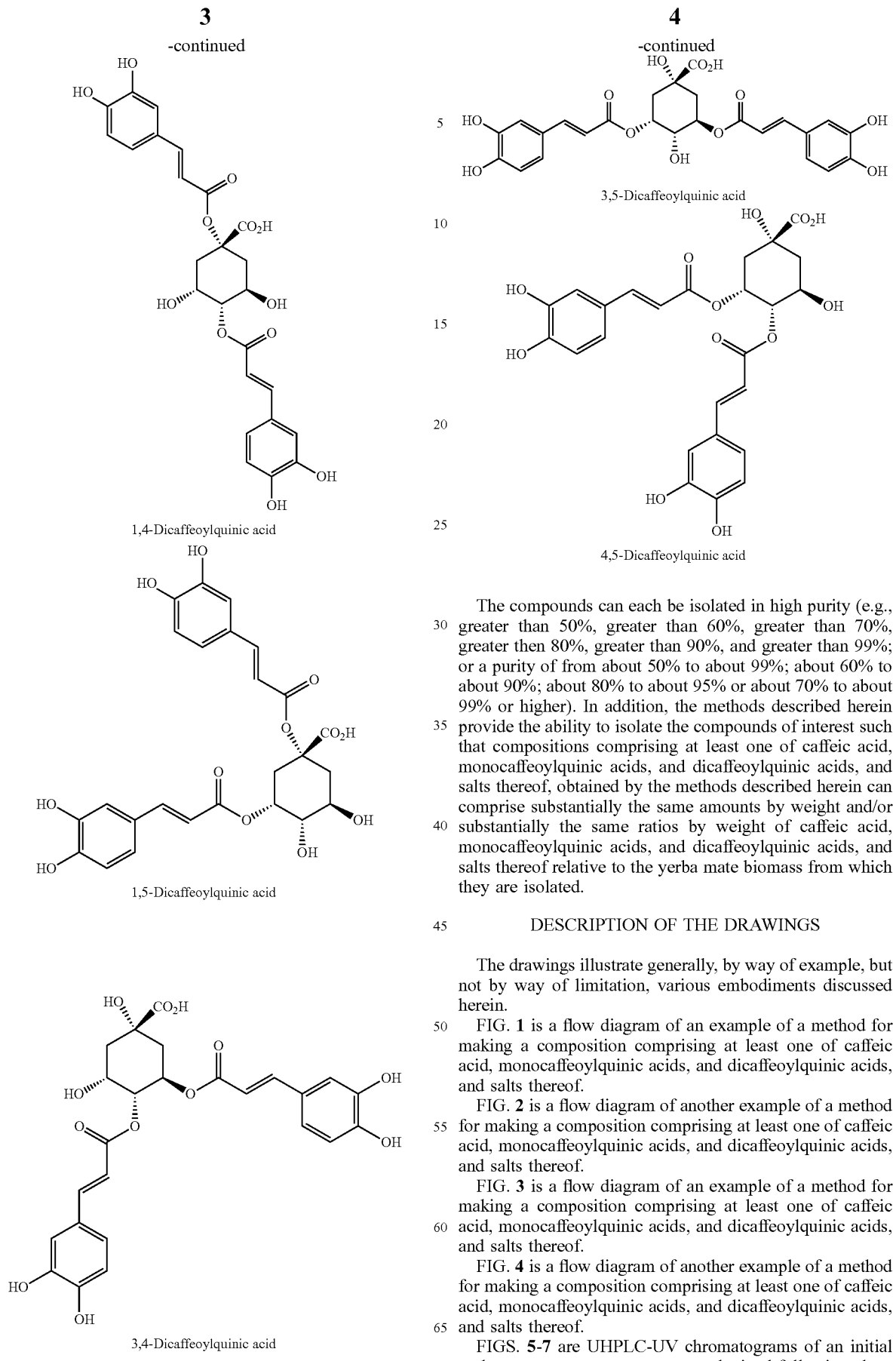

The compounds can each be isolated in high purity (e.g., greater than 50%, greater than 60%, greater than 70%, greater then 80%, greater than 90%, and greater than 99%; or a purity of from about 50% to about 99%; about 60% to about 90%; about 80% to about 95% or about 70% to about 99% or higher). In addition, the methods described herein provide the ability to isolate the compounds of interest such that compositions comprising at least one of caffeic acid, monocaffeoylquinic acids, and dicaffeoylquinic acids, and salts thereof, obtained by the methods described herein can comprise substantially the same amounts by weight and/or substantially the same ratios by weight of caffeic acid, monocaffeoylquinic acids, and dicaffeoylquinic acids, and salts thereof relative to the yerba mate biomass from which they are isolated.

DESCRIPTION OF THE DRAWINGS

The drawings illustrate generally, by way of example, but not by way of limitation, various embodiments discussed herein.

FIGS. 8-10 are tables showing, in tabular form, the peak name, retention time, and relative area percent data for the UHPLC-UV chromatographs shown in FIGS. 5-7, respectively.

FIG. 8 is a table of the data for an initial yerba mate extract. The sum of target compounds is 49.7% purity by UV absorbance at 210 nm.

FIG. 9 is a table of the data for a concentrate obtained following chromatographing the adjusted second initial extract on an ion exchange chromatography stationary phase. The sum of target compounds is 87.1% purity by UV absorbance at 210 nm.

FIG. 10 is the data after drying, following the process described in steps (a)-(h), described herein, where "DCQA" refers to "dicaffeoylquinic acid." The sum of target compounds is 93.2% purity by UV absorbance at 210 nm.

Figure 1:
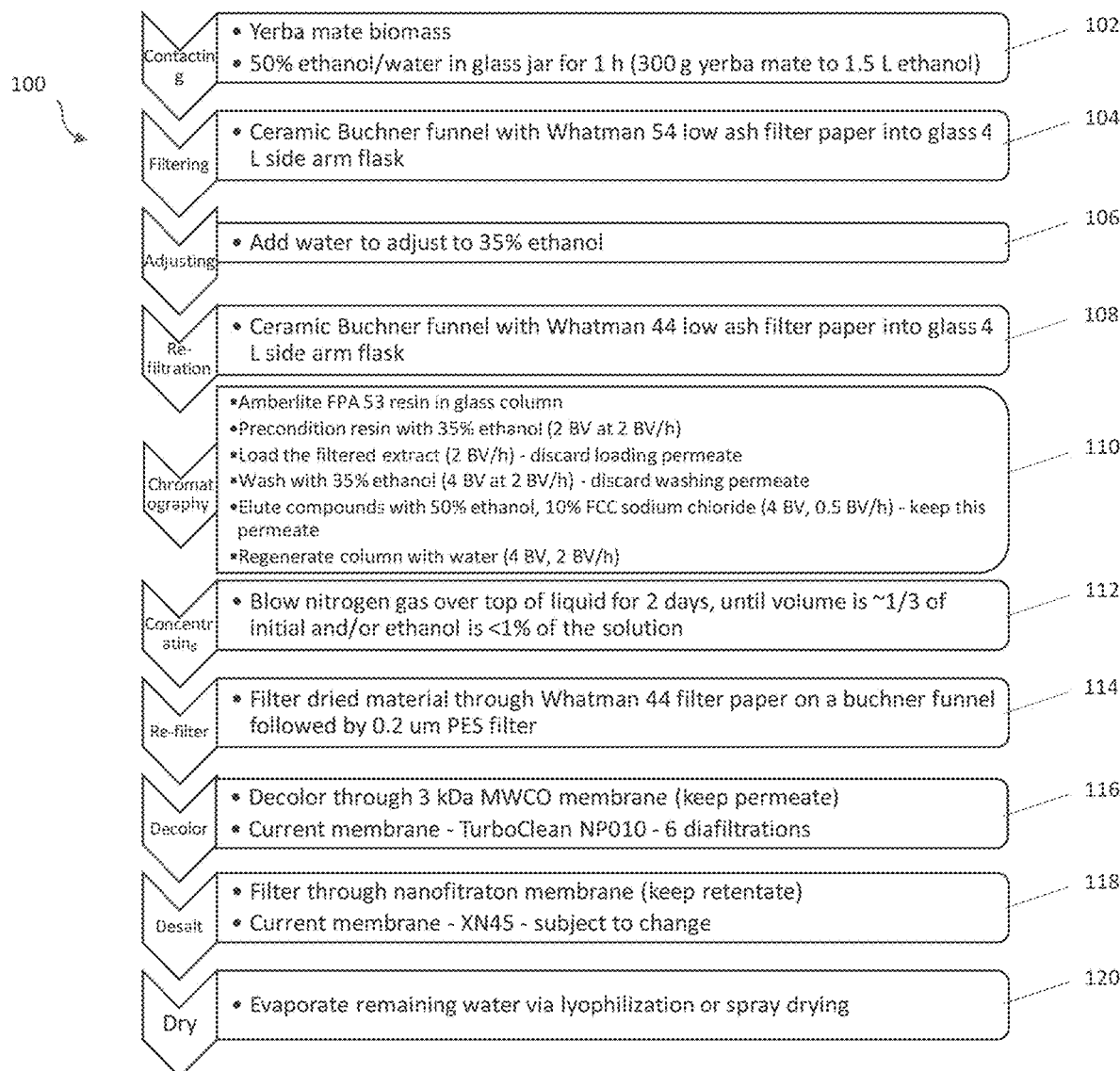
FIG. 1 is a flow diagram of an example of a method for making a composition comprising at least one of caffeic acid, monocaffeoylquinic acids, and dicaffeoylquinic acids, and salts thereof.
Figure 2:
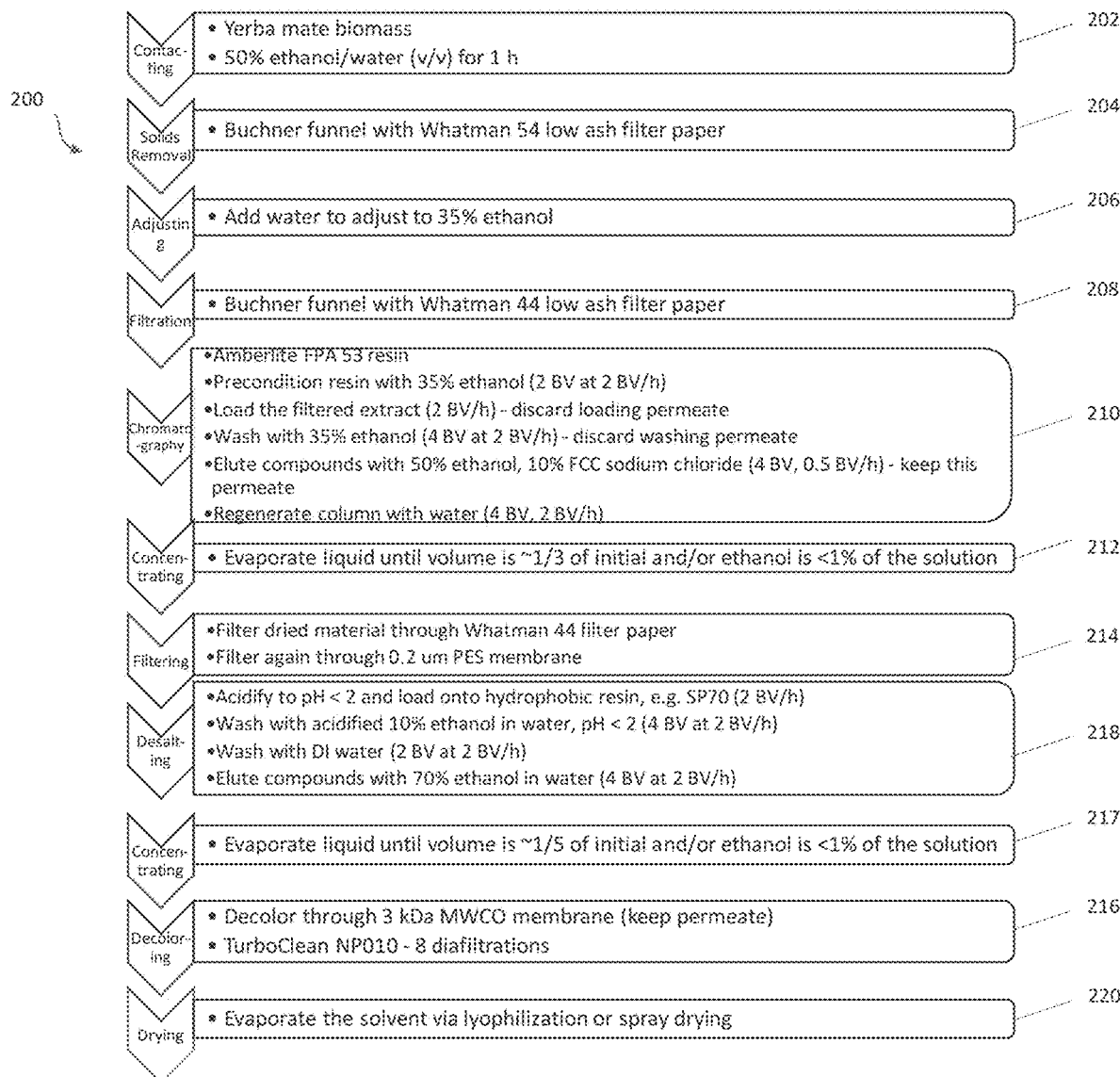
FIG. 2 is a flow diagram of another example of a method for making a composition comprising at least one of caffeic acid, monocaffeoylquinic acids, and dicaffeoylquinic acids, and salts thereof.
Figure 3:
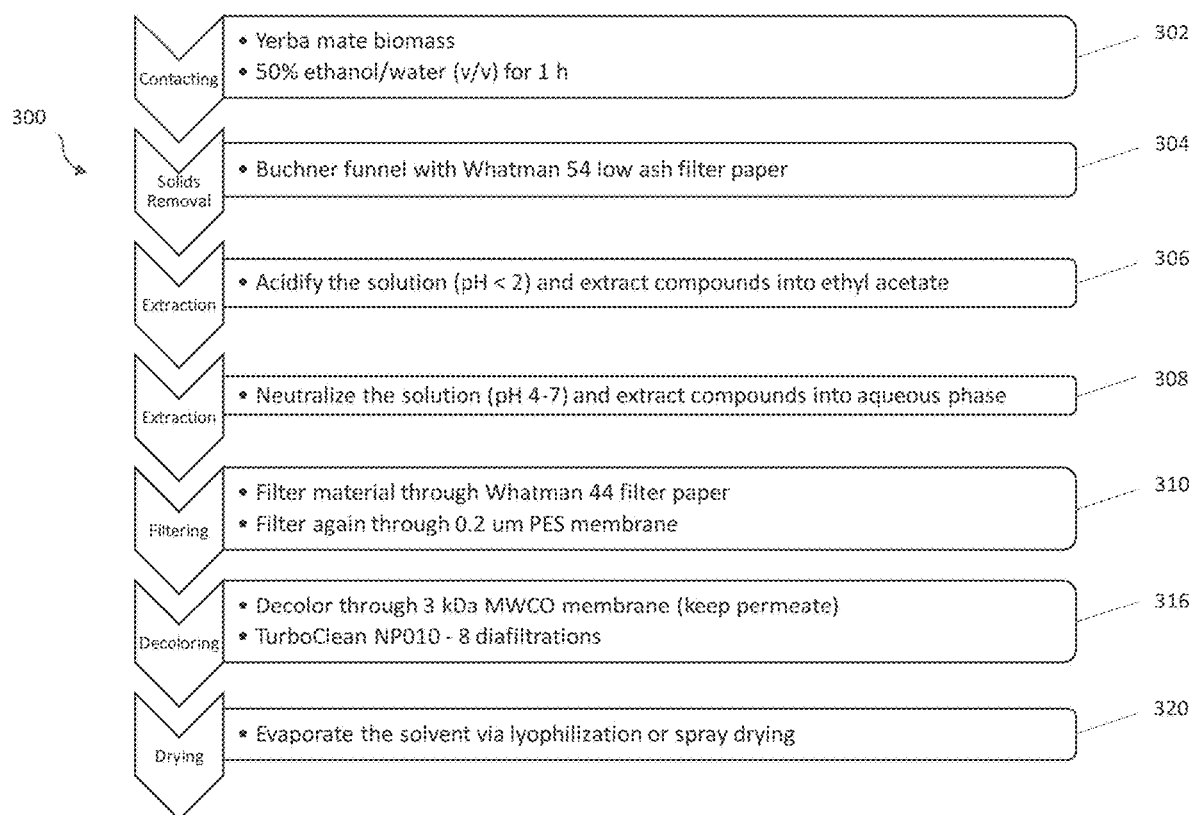
FIG. 3 is a flow diagram of an example of a method for making a composition comprising at least one of caffeic acid, monocaffeoylquinic acids, and dicaffeoylquinic acids, and salts thereof.
Figure 4:
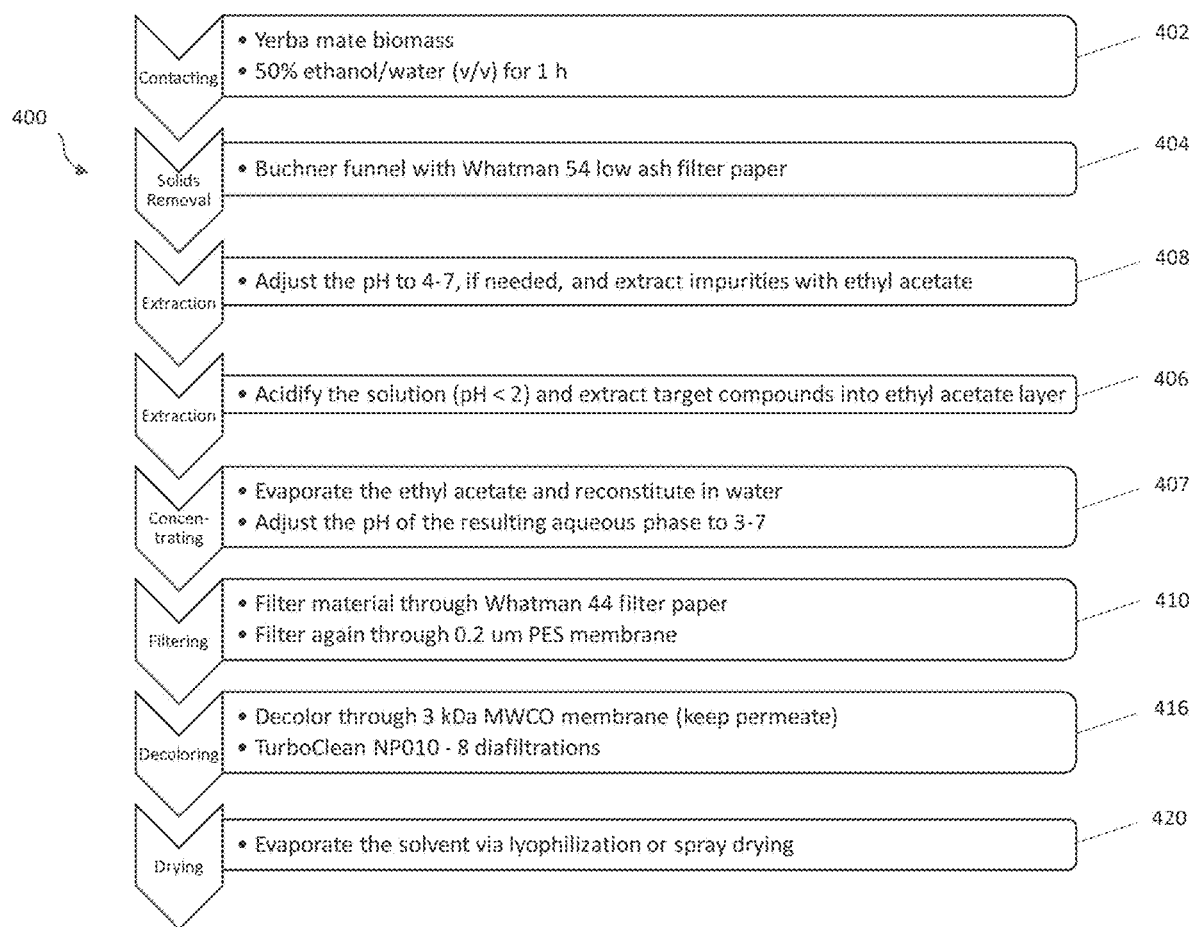
FIG. 4 is a flow diagram of another example of a method for making a composition comprising at least one of caffeic acid, monocaffeoylquinic acids, and dicaffeoylquinic acids, and salts thereof.

Repeated use of reference characters in the specification and drawings is intended to represent the same or analogous features or elements of the disclosure, even when the numbers increase by 100 from figure-to-figure (e.g., drying operation 120 in FIG. 1 is analogous to or the same as drying operations 220, 320, and 420 in FIGS. 2-4, respectively). It should be understood that numerous other modifications and examples can be devised by those skilled in the art, which fall within the scope and spirit of the principles of the disclosure.

DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The disclosure relates generally to methods of making compositions comprising at least one of caffeic acid, monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof from yerba mate biomass. Because the caffeic acid, monocaffeoylquinic acids, and dicaffeoylquinic acids can be considered weak acids, they can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the caffeic acid, monocaffeoylquinic acids, and dicaffeoylquinic acids will depend on various factors, including the $pK_a$ of each compound and the pH of the composition.

Examples of salts of caffeic acid, monocaffeoylquinic acids, and dicaffeoylquinic acids include, but are not limited to, quaternary ammonium, sodium, potassium, lithium, magnesium, and calcium salts of caffeic acid, monocaffeoylquinic acids, and dicaffeoylquinic acids, and the like.

An example of a method for making a composition comprising at least one of caffeic acid, monocaffeoylquinic acids, and dicaffeoylquinic acids, and salts thereof, the method comprising (a) contacting yerba mate biomass with an aqueous composition to obtain an initial extract;
(b) removing solids from the initial extract to obtain a second initial extract;
(c) adjusting the volume of the second initial extract with an aqueous composition to obtain an adjusted second initial extract;
(d) chromatographing the adjusted second initial extract on an ion exchange chromatography stationary phase;
(e) eluting the ion exchange chromatography stationary phase to obtain a first eluent comprising a solvent;
(f) removing the solvent to form a concentrate; and
(g) at least one of decoloring and desalting the concentrate to at least one of a filtrate and a retentate.

An example of a method for making a composition comprising at least one of caffeic acid, monocaffeoylquinic acids, and dicaffeoylquinic acids, and salts thereof, the method comprising (a) contacting yerba mate biomass with an aqueous composition to obtain an initial extract;
(b) removing solids from the initial extract to obtain a second initial extract;
(c) adjusting the volume of the second initial extract with an aqueous composition to obtain an adjusted second initial extract;
(d) chromatographing the adjusted initial extract on an ion exchange chromatography stationary phase;
(e) eluting the ion exchange stationary phase to obtain a first eluent comprising a solvent;
(f) removing the solvent to form a concentrate;
(g) at least one of decoloring and desalting the concentrate to obtain at least one of a filtrate and a retentate; and
(h) drying the at least one of a filtrate and a retentate to obtain the composition comprising at least one of caffeic acid, monocaffeoylquinic acids, and dicaffeoylquinic acids, and salts thereof.

Step (a) of the methods described herein involve contacting yerba mate biomass with an aqueous composition to obtain an initial extract comprising at least one of caffeic acid, monocaffeoylquinic acids, and dicaffeoylquinic acids, and salts thereof (e.g., quaternary ammonium, sodium, potassium, lithium, magnesium, and calcium salts).

The aqueous composition can comprise water and not contain any co-solvents, such as organic solvents. But the aqueous composition can comprise co-solvents, in addition to water. Suitable co-solvents include organic solvents, such as, $(C_1-C_4)$alkanols and mixtures of $(C_1-C_4)$alkanols. By "$(C_1-C_4)$alkanol" is meant an alcohol of the formula $(C_1-C_4)$alkyl-OH, wherein "alkyl" refers to straight chain and branched alkyl groups having from 1 to 4 carbon atoms such as methyl, ethyl, n-propyl, n-butyl, isopropyl, iso-butyl, sec-butyl, and t-butyl, such that the resulting $(C_1-C_4)$alkanol is methanol, ethanol, n-propanol, n-butanol, isopropanol, iso-butanol, sec-butanol, and t-butanol. The proportion of organic solvent, such as $(C_1-C_4)$alkanol or mixtures of $(C_1-C_4)$alkanols, can be any suitable proportion such that the aqueous composition can comprise up to about 30%, up to about 40%, up to about 50% or up to about 60%, up to about 70%, up to about 80%, up to about 90% or up to 100% by volume organic solvent the balance being water, except when the aqueous composition comprises 100% by volume organic solvent; or from about 30% to about 100%, about 50% to about 100%, about 60% to about 90%, about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively pure water made basic to pH 7-11 with hydroxide, such as with sodium or potassium hydroxide, can be useful in the aqueous composition, with or without a co-solvent. In still other instances, it may be suitable to add a suitable non-ionic solute that can help balance the osmotic potential of the aqueous composition.

As used herein, the term "yerba mate biomass" generally refers to any and all parts of the yerba mate plant, such as *Ilex paraguariensis*, including the yerba mate plant leaves, stalks, stems, tops, roots, and the like. The yerba mate biomass can be in any suitable form including in comminuted form resulting from, e.g., from chopping the yerba mate biomass prior to and/or during the contacting with the aqueous composition. For example, the yerba mate biomass can be comminuted in a suitable container and the aqueous composition can be added to the comminuted yerba mate biomass, thus "contacting" the yerba mate biomass. The comminuted yerba mate biomass can then be optionally further comminuted within the suitable container. Or the yerba mate biomass can be placed in a suitable container, to which the aqueous composition is added, thus "contacting" the yerba mate biomass, and the resulting composition can be comminuted.

The yerba mate biomass can be stirred, sonicated or otherwise agitated prior to and/or during the contacting to, among other things, maximize the extraction of the at least one of caffeic acid, monocaffeoylquinic acids, and dicaffeoylquinic acids, and salts thereof.

The initial extract can be carried through to step (c) as-is or bulk solids and or plant solids present, such as comminuted yerba mate plant leaves, stalks, tops, roots, and the like, can be removed in step (b) of the methods described herein. When step (b) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of caffeic acid, monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Step (c) of the methods described herein involves adjusting the volume of the initial extract or second initial extract with a first aqueous composition or a second aqueous composition, respectively, to obtain an adjusted initial extract or adjusted second initial extract. The first and second aqueous compositions can be different or the same. The adjusted initial extract or adjusted second initial extract can be filtered at this point or can be carried through to step (d) as-is. The initial extract or the second initial extract can be filtered using any suitable filtration method, including gravity filtration or vacuum filtration through any suitable filter, so long as the filter does not substantially retain the at least one of caffeic acid, monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

The volume of the initial extract or second initial extract can be adjusted with a sufficient amount of an aqueous composition (e.g., water) to obtain an adjusted initial extract or adjusted second initial extract to, among other things, increase the binding of the at least one of caffeic acid, monocaffeoylquinic acids, and dicaffeoylquinic acids, and salts thereof, to the ion exchange chromatography column used in step (d) of the methods described herein, relative to an unadjusted initial extract or an unadjusted second initial extract.

The volume of the initial extract or second initial extract can be adjusted to, among other things, adjust the amount of organic solvent, when present, in the initial extract or second initial extract. The volume of the initial extract or second initial extract can be adjusted such that the adjusted initial extract or adjusted second initial extract comprises less than about 60%, less than about 50%, less than about 40%, less than about 30%, less than about 20%, less than about 10%, less than about 5%, less than about 1% or even about 0% by volume organic solvent, the balance being water; or from about 0% to about 40%, about 0% to about 30%, about 10% to about 40%, about 10% to about 30%, about 20% to about 40%, about 30% to about 40%, or about 35% by volume organic solvent, the balance being water.

Step (d) of the methods described herein involves chromatographing the adjusted initial extract or the second initial extract on an ion exchange stationary phase (e.g., a weak anion exchange stationary phase). The chromatographing can be performed in any suitable fashion, including in batch mode or using a column. The chromatographing can be performed with an aqueous composition (e.g., an aqueous composition comprising a ($C_1$-$C_4$)alkanol) as eluent (e.g., an aqueous composition comprising from about 0% to about 40%, about 0% to about 30%, about 10% to about 40%, about 10% to about 30%, about 20% to about 40%, about 30% to about 40%, or about 35% by volume ($C_1$-$C_4$)alkanol, the balance being water), leaving the at least one of caffeic acid, monocaffeoylquinic acids, and dicaffeoylquinic acids, and salts thereof, adsorbed on the weak ion exchange chromatography column, while eluting other compounds including caffeine, rutin (also known as rutoside, quercetin-3-O-rutinoside, and sophorin)

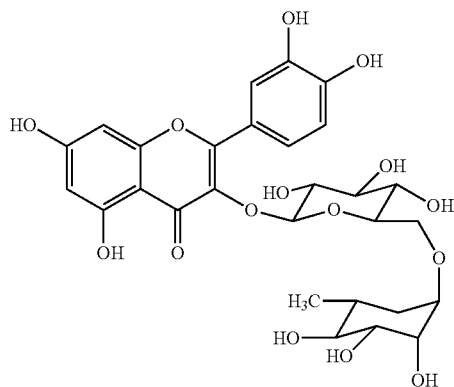 [SMILES: CC1CC(OCC2OC(Oc3c(-c4ccc(O)c(O)c4)oc4cc(O)cc(O)c4c3=O)C(O)C(O)C2O)C(O)C(O)C1O]

and isomers thereof. Step (d) of the methods described herein can decrease the concentration of at least one of caffeine, rutin, and rutin isomers to a concentration of less than 1%, less than 0.5%, less than 0.1%, less than 0.05%, less than 0.01% or less than 0.001% by mass. The instant disclosure therefore contemplates yerba mate extracts comprising less than 0.1% of at least one of caffeine, rutin, and rutin isomers by mass. The instant disclosure also contemplates yerba mate extracts comprising less than 0.5% by mass of each one of caffeine, rutin, and rutin isomers and a less than about 1% by mass of caffeine, rutin, and rutin isomers combined. The instant disclosure also contemplates yerba mate extracts that are effectively free of at least one of caffeine, rutin, and rutin isomers (e.g., free of caffeine, free of rutin, free of rutin isomers, and/or free of caffeine, rutin, and rutin isomers).

The ion exchange stationary phase is non-limiting and can be any suitable ion exchange chromatography stationary phase. Examples of suitable ion exchange chromatography stationary phases include ANX-SEPHAROSE® fast flow resin, DEAE SEPHAROSE®, DEAE SEPHADEX® A25 resin, AMBERLITE® (FPA 53; FPA 55; CG-50 Type I; IRC-50; IRC-50S; and IRP-64), DIAION WA10, and DOWEX® CCR-3.

The ion exchange chromatography stationary phase can optionally be pre-conditioned with an aqueous composition (e.g., an aqueous composition comprising a $(C_1-C_4)$alkanol), such as an aqueous composition comprising from about 0% to about 40%, about 0% to about 30%, about 10% to about 40%, about 10% to about 30%, about 20% to about 40%, about 30% to about 40%, or about 35% by volume $(C_1-C_4)$alkanol, the balance being water, prior to the chromatographing of the adjusted initial extract or adjusted second initial extract. For example, the weak ion exchange chromatography column can be pre-conditioned with about 2 or more bed volumes (BV) at a flow rate of about 2 BV/h.

The pH of the weak ion exchange chromatography column can optionally be adjusted prior to the chromatographing of the adjusted initial extract or adjusted second initial extract. For example, the pH of the weak ion exchange chromatography column can be adjusted prior to the chromatographing with any suitable acid (e.g., hydrochloric acid) such that the pH of the weak ion exchange chromatography column (e.g., the pH of the resin/stationary phase) is a pH of less than about 10, about 9 or less, about 8 or less, about 7 or less, about 6 or less, about 5 or less, about 4 or less, about 3 or less; or a pH of about 2 to about 10, about 3 to about 8, about 5 to about 9, about 2 to about 6; about 3 to about 4; or about 3 to about 6. The pH of the weak ion exchange chromatography column can be adjusted before or after the column is optionally pre-conditioned with the aqueous composition comprising a $(C_1-C_4)$ prior to the chromatographing of the adjusted initial extract or adjusted second initial extract.

After pre-conditioning and/or adjusting of the pH of the weak ion exchange chromatography column, the adjusted initial extract or adjusted second initial extract can be loaded onto the column at any suitable rate, such as at a rate of above 2 BV/h (bed volumes per hour). After loading the adjusted initial extract or adjusted second initial extract, the column can be washed with any suitable volume of an aqueous composition comprising a $(C_1-C_4)$alkanol (e.g., at least about 2 BV, at least about 3 BV or at least about 4 BV of an aqueous composition comprising from about 10% to about 40%, about 10% to about 30%, about 20% to about 40%, about 30% to about 40%, or about 35% by volume $(C_1-C_4)$alkanol, the balance being water) at any suitable rate, such as at a rate of about 2 BV/h. The volume of aqueous composition comprising a $(C_1-C_4)$alkanol can be discarded, as it will contain, among other things, caffeine, rutin, and rutin isomers.

Step (e) of the methods described herein involves eluting the adsorbed at least one of caffeic acid, monocaffeoylquinic acids, and dicaffeoylquinic acids, and salts thereof, from the weak ion exchange chromatography column to obtain a first eluent comprising the at least one of caffeic acid, monocaffeoylquinic acids, and dicaffeoylquinic acids, and salts thereof. The eluting is performed under any conditions suitable to elute the at least one of caffeic acid, monocaffeoylquinic acids, and dicaffeoylquinic acids, and salts thereof from the column.

An example of suitable conditions to elute the at least one of caffeic acid, monocaffeoylquinic acids, and dicaffeoylquinic acids, and salts thereof from the column include eluting the column with any suitable volume of a solution comprising a salt (e.g., sodium chloride, potassium chloride, ammonium chloride, sodium sulfate, potassium sulfate, sodium phosphate, potassium phosphate, and the like). Examples of solutions comprising a salt include solutions comprising at least one salt (e.g., about 5 wt. % to about 25 wt. %, about 15 wt. % to about 20 wt. % or about 5 wt. % to about 10 wt. % of a salt) dissolved in an aqueous composition comprising a $(C_1-C_4)$alkanol (e.g., at least about 2 BV, at least about 3 BV or at least about 4 BV of an aqueous composition comprising from about 10% to about 60%, about 20% to about 50%, about 30% to about 55%, about 40% to about 60%, or about 50% by volume $(C_1-C_4)$alkanol).

Another example of suitable conditions to elute the at least one of caffeic acid, monocaffeoylquinic acids, and dicaffeoylquinic acids, and salts thereof from the column include eluting the column with any suitable volume of a solution comprising an acid (e.g., hydrochloric acid, sulfuric acid, phosphoric acid, acetic acid, formic acid, and the like). Examples of solutions comprising an acid include solutions comprising hydrochloric acid and the like and optionally acids solutions comprising an aqueous composition comprising from about 10% to about 60%, about 20% to about 50%, about 30% to about 55%, about 40% to about 60%, or about 50% by volume $(C_1-C_4)$alkanol).

The first eluent comprising the at least one of caffeic acid, monocaffeoylquinic acids, and dicaffeoylquinic acids, and salts thereof, collected from the eluting step is collected and can be subsequently concentrated by removing solvent (e.g., to remove water and $(C_1-C_4)$alkanol) by any suitable means to provide a concentrate comprising the at least one of caffeic acid, monocaffeoylquinic acids, and dicaffeoylquinic acids, and salts thereof. The solvent removal can be accomplished under an inert atmosphere (e.g., under a nitrogen gas atmosphere). While not wishing to be bound by any specific theory, it is believed that performing the solvent removal under an inert atmosphere can reduce the formation of highly colored polymeric substances that either natively exist in the yerba mate biomass or form at one or more of the steps described herein.

The first eluent comprising the at least one of caffeic acid, monocaffeoylquinic acids, and dicaffeoylquinic acids, and salts thereof comprises a solvent. The solvent can be removed in a step (f) to dryness or it can be removed to a point where a volume of an aqueous composition comprising a $(C_1-C_4)$alkanol remains as a solvent (e.g., about 50%, about 40%, about 30% about 20%, about 10% or about 5% of an original, total volume of the eluent) to form a concentrate, though the ratio of components that make up the aqueous composition comprising a $(C_1-C_4)$alkanol may or may not be different from the ratio of components that made up the aqueous composition comprising a ($C_1$-$C_4$)alkanol that was used to elute the adsorbed at least one of caffeic acid, monocaffeoylquinic acids, and dicaffeoylquinic acids, and salts thereof. Alternatively, the solvent in the eluent comprising the at least one of caffeic acid, monocaffeoylquinic acids, and dicaffeoylquinic acids, and salts thereof, can be removed to a point where a volume of an aqueous composition comprising a ($C_1$-$C_4$)alkanol remains, wherein the aqueous composition comprising a ($C_1$-$C_4$)alkanol comprises less than about 10%, less than about 5%, less than about 2% or less than about 1% by volume ($C_1$-$C_4$)alkanol.

Suitable conditions for removing solvent from the eluent comprising the at least one of caffeic acid, monocaffeoylquinic acids, and dicaffeoylquinic acids, and salts thereof, to form a concentrate comprising the at least one of caffeic acid, monocaffeoylquinic acids, and dicaffeoylquinic acids, and salts thereof include blowing an inert gas (e.g., nitrogen gas) over the surface of the eluent. The eluent can be heated while blowing the nitrogen gas or it can be at room temperature (e.g., 25° C.). Other conditions for removing the solvent in the eluent include applying a vacuum to the container containing the eluent. The vacuum can be applied with the eluent at room temperature or while heating the container. Yet other conditions for removing solvent in the eluent include passing the eluent through a wiped film evaporator or an agitated thin film evaporator.

The pH of the concentrate can be adjusted at this point to obtain a pH-adjusted concentrate, though adjusting the pH at this point is optional. For example, the pH of the concentrate can be adjusted to a pH where the at least one of caffeic acid, monocaffeoylquinic acids, and dicaffeoylquinic acids, and salts thereof are protected from degradation. Suitable pHs include pHs of less than about 6, less than about 5, less than about 4, less than about 3 or less than about 2; such as a pH of from about 2 to about 6, about 2 to about 5, about 2 to about 4, about 3 to about 5 or a pH of about 3.5. The pH of the concentrate can be adjusted by using any suitable acid or base. When an acid is used, the acid can be hydrochloric acid and the like.

The concentrate or the pH-adjusted concentrate can be taken on as-is in the methods described herein or the removing step (f) or they can be filtered. The concentrate or the pH-adjusted concentrate can be filtered using any suitable filter (e.g., low ash filter paper, such as Whatman 44 or 54 low ash filter paper), a nylon filter, a polyethersulfone filter, a glass fiber filter, a pad of diatomaceous earth, and the like. In some instances, the pH-adjusted concentrate can be filtered through a polymeric membrane, such as a polyethersulfone (PES) filter having, e.g., 0.2 µm pore size, or a pleated (flat membrane, vacuum filtration) or a pleated PES membrane, depending on the volume of the concentrate or the pH-adjusted concentrate.

The concentrate comprising the at least one of caffeic acid, monocaffeoylquinic acids, and dicaffeoylquinic acids, and salts thereof, whether it is pH-adjusted, filtered or both pH-adjusted and filtered, can be taken directly to drying step (h) or can be submitted for desalting/decoloring in step (g) (in either order, including desalting, followed by decoloring; decoloring, followed by desalting; decoloring, but not desalting; or desalting, but not decoloring) of a concentrate that can be highly colored. The desalting/decoloring can be accomplished under an inert atmosphere (e.g., under a nitrogen gas atmosphere). While not wishing to be bound by any specific theory, it is believed that performing the one or more steps under an inert atmosphere can reduce the formation of highly colored polymeric substances that either natively exist in the yerba mate biomass or form at one or more of the steps described herein.

The concentrate, whether it is pH-adjusted, filtered or both pH-adjusted and filtered, can be decolored by any suitable means, including ultrafiltration (e.g., filtering through a molecular weight cutoff membrane, size-exclusion chromatography or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the yerba mate biomass or form at one or more of the steps described herein.

The filtrate from decoloring can be taken on to drying step (h) or it can be desalted in step (g). Alternatively, the concentrate, whether it is pH-adjusted, filtered or both pH-adjusted and filtered, can be desalted without first decoloring. Regardless, the desalting can be accomplished using a nanofiltration membrane and a hydrophobic resin. Those of skill in the art would recognize that when one uses a nanofiltration membrane and a hydrophobic resin one discards the permeate and keeps the retentate. In one example, desalting can be accomplished using a hydrophobic resin (e.g., a porous poly divinylbenzene/ethylvinylbenzene matrix, such as SEPABEADS™ SP70), where one would load a pH-adjusted concentrate (e.g., an acidified concentrate, with a pH of less than about 2) comprising less than about 20% by volume ($C_1$-$C_4$)alkanol. The resin is then washed with dilute alcohol (e.g., less than about 10% by volume ($C_1$-$C_4$)alkanol, the rest being water having a pH of less than about 2) and then eluted with an aqueous composition comprising about 70% by volume ($C_1$-$C_4$)alkanol in water to obtain a desalted second eluent comprising the at least one of caffeic acid, monocaffeoylquinic acids, and dicaffeoylquinic acids, and salts thereof.

If desalting precedes decoloring in step (g), the solvent in the permeate from the desalting step can be removed to a point where a volume of an aqueous composition comprising a ($C_1$-$C_4$)alkanol remains as a solvent (e.g., about 50%, about 40%, about 30% about 20%, about 10% or about 5% of an original, total volume of the eluent) to form a first desalted concentrate. Alternatively, the solvent in the permeate from the desalting can be removed, to give a second desalted concentrate, to a point where a volume of an aqueous composition comprising a ($C_1$-$C_4$)alkanol remains, wherein the aqueous composition comprising a ($C_1$-$C_4$) alkanol comprises less than about 10%, less than about 5%, less than about 2% or less than about 1% by volume ($C_1$-$C_4$)alkanol. The first desalted concentrate can also have the attributes of the second desalted concentrate, such that the first desalted concentrate also has less than about 10%, less than about 5%, less than about 2% or less than about 1% by volume ($C_1$-$C_4$)alkanol.

Suitable conditions for removing solvent from the permeate comprising the at least one of caffeic acid, monocaffeoylquinic acids, and dicaffeoylquinic acids, and salts thereof, to form a first/second desalted concentrate comprising the at least one of caffeic acid, monocaffeoylquinic acids, and dicaffeoylquinic acids, and salts thereof include blowing an inert gas (e.g., nitrogen gas) over the surface of the eluent. The permeate can be heated while blowing the nitrogen gas or it can be at room temperature (e.g., 25° C.). Other conditions for removing the solvent in the eluent include applying a vacuum to the container containing the permeate. The vacuum can be applied with the permeate at room temperature or while heating the container. Yet other conditions for removing solvent in the permeate include passing the permeate through a wiped film evaporator or an agitated thin film evaporator.

In another example, the concentrate comprising the at least one of caffeic acid, monocaffeoylquinic acids, and dicaffeoylquinic acids, and salts thereof can be filtered through filter paper to obtain a first filtrate, the first filtrate is ultrafiltered to obtain a second filtrate, and the second filtrate is nanofiltered using a nanofiltration membrane to obtain a first retentate or the second filtrate is eluted through a hydrophobic resin to obtain a desalted second eluent. In another example, the concentrate comprising the at least one of caffeic acid, monocaffeoylquinic acids, and dicaffeoylquinic acids, and salts thereof can be filtered through filter paper to obtain a first filtrate, the first filtrate is nanofiltered using a nanofiltration membrane to obtain a third retentate or the first filtrate is eluted through a hydrophobic resin to obtain a desalted second eluent, and the third retentate or the desalted second eluent is ultrafiltered to obtain a third filtrate.

As mentioned herein, the eluent comprising the at least one of caffeic acid, monocaffeoylquinic acids, and dicaffeoylquinic acids, and salts thereof, can be concentrated to dryness or it can be concentrated to a point where a volume of an aqueous composition comprising a $(C_1-C_4)$ alkanol remains. If the eluent is concentrated to dryness, the dry material can be reconstituted using, for example, an aqueous composition comprising a $(C_1-C_4)$alkanol. The reconstituted material can then be filtered as described herein, to among other things, at least one of desalt and decolor.

The methods described herein can include step (h) that involves drying first retentate, desalted second eluent or the third filtrate to obtain the composition comprising the at least one of caffeic acid, monocaffeoylquinic acids, and dicaffeoylquinic acids, and salts thereof. The first retentate, desalted second eluent or the third filtrate can be dried in any suitable manner, including by lyophilization or spray drying.

FIG. 1 is a flow diagram of a method 100 for making a composition comprising at least one of caffeic acid, monocaffeoylquinic acids, and dicaffeoylquinic acids, and salts thereof. In operation 102, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 104, the initial extract is filtered using, for example, a ceramic Büchner funnel with Whatman 54 low ash filter paper into glass 4 L side arm flask. In operation 106, the volume of the filtered initial extract is adjusted with an aqueous composition, in this case water, to obtain an adjusted filtered initial extract containing a lower proportion of ethanol, in this case 35% by volume ethanol. In operation 108, the adjusted filtered initial extract can be re-filtered using, for example, a ceramic Büchner funnel with Whatman 44 low ash filter paper into glass 4 L side arm flask. In operation 110, the adjusted filtered initial extract is chromatographed on an ion exchange chromatography stationary phase. For example, AMBERLITE® FPA 53 resin is packed in glass column. The resin is preconditioned with 35% ethanol (2 BV at 2 BV/h). The adjusted filtered initial extract is loaded is loaded (2 BV/h) onto the resin, discarding the loading permeate. The resin is washed with 35% ethanol (4 BV at 2 BV/h) discarding the washing permeate. The at least one of caffeic acid, monocaffeoylquinic acids, and dicaffeoylquinic acids, and salts thereof are eluted with 50% ethanol/water, 10% FCC sodium chloride (4 BV, 0.5 BV/h) and the permeate is kept. The column/resin can optionally be regenerated with water (4 BV, 2 BV/h). In operation 112, the eluent/permeate is concentrated to form a concentrate. In this case, nitrogen gas was blown over the top of the eluent/permeate for 2 days, until volume the volume is approximately one third of the initial volume of eluent/permeate and/or ethanol is less than 1% in the eluent/permeate, thereby obtaining a concentrate. In operation 114, the concentrate is acidified to a pH of approximately 3.5 and then filtered through a Whatman 44 filter paper on a Büchner funnel followed by 0.2 µm polyether sulfone (PES) filter. In operation 116, the filtered concentrate is decolored using a molecular weight cutoff membrane (MWCO; e.g., a MWCO membrane that removes materials having a molecular weight of greater than 10 kDA, such as a 3 kDa TURBO-CLEAN® NP010) to, among other things, decolor the filtered concentrate and obtain a permeate. In operation 118, the permeate is filtered through a nanofiltration membrane (e.g., TRISEP® XN45 membrane) and the retentate is subsequently dried in operation 120 to obtain the composition comprising at least one of caffeic acid, monocaffeoylquinic acids, and dicaffeoylquinic acids, and salts thereof.

FIG. 2 is a flow diagram of a method 200 for making a composition comprising at least one of caffeic acid, monocaffeoylquinic acids, and dicaffeoylquinic acids, and salts thereof. In operation 202, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 204, the initial extract is filtered using, for example, a ceramic Büchner funnel with Whatman 54 low ash filter paper into glass 4 L side arm flask. In operation 206, the volume of the filtered initial extract is adjusted with an aqueous composition, in this case water, to obtain an adjusted filtered initial extract containing a lower proportion of ethanol, in this case 35% by volume ethanol. In operation 208, the adjusted filtered initial extract can be re-filtered using, for example, a ceramic Büchner funnel with Whatman 44 low ash filter paper into glass 4 L side arm flask. In operation 210, the adjusted filtered initial extract is chromatographed on an ion exchange chromatography stationary phase. For example, AMBERLITE® FPA 53 resin is packed in glass column. The resin is preconditioned with 35% ethanol (2 BV at 2 BV/h). The adjusted filtered initial extract is loaded is loaded (2 BV/h) onto the resin, discarding the loading permeate. The resin is washed with 35% ethanol (4 BV at 2 BV/h) discarding the washing permeate. The at least one of caffeic acid, monocaffeoylquinic acids, and dicaffeoylquinic acids, and salts thereof are eluted with 50% ethanol/water, 10% FCC sodium chloride (4 BV, 0.5 BV/h) and the permeate is kept. The column/resin can optionally be regenerated with water (4 BV, 2 BV/h). In operation 212, the eluent/permeate is concentrated to form a concentrate, where the volume is approximately one third of the initial volume of eluent/permeate and/or ethanol is less than 1% in the eluent/permeate, thereby obtaining a concentrate. In operation 214, the concentrate is acidified to a pH of approximately 1 and then filtered through a Whatman 44 filter paper on a Büchner funnel followed by 0.2 µm polyether sulfone (PES) filter. In operation 218, the concentrate is desalted using a hydrophobic resin (e.g., a porous poly divinylbenzene/ethylvinylbenzene matrix, such as SEPABEADS™ SP70) and the solvent in the retentate is removed in operation 217. In operation 216, the desalted concentrate is decolored using a molecular weight cutoff membrane (MWCO; e.g., a MWCO membrane that removes materials having a molecular weight of greater than 10 kDA, such as a 3 kDa TURBOCLEAN® NP010) to, among other things, decolor the filtered concentrate and obtain a permeate. subsequently dried in operation 220 to obtain the composition comprising at least one of caffeic acid, monocaffeoylquinic acids, and dicaffeoylquinic acids, and salts thereof.

Another example of a method for making a composition comprising at least one of caffeic acid, monocaffeoylquinic acids, and dicaffeoylquinic acids, and salts thereof, the method comprising
(i) contacting yerba mate biomass with an aqueous composition to obtain an initial extract;
(ii) removing solids from the initial extract to obtain a second initial extract;
(iii) contacting the second initial extract with acidified ethyl acetate to obtain an acidic ethyl acetate extract;
(iv) neutralizing the acidic ethyl acetate extract to obtain neutralized ethyl acetate and an aqueous extract;
(v) decoloring the aqueous extract to obtain a decolored aqueous extract; and
(vi) drying the decolored aqueous extract to obtain the composition comprising at least one of caffeic acid, monocaffeoylquinic acids, and dicaffeoylquinic acids, and salts thereof.

Steps (i), (ii), and (vi) are performed as described herein for steps (a), (b), and (h). Step (v) is analogous to filtering step (g), except that step (v) involves only decoloring processes, such as ultrafiltration, which includes filtering through a molecular weight cutoff membrane, size-exclusion chromatography, and gel permeation, as discussed herein. Accordingly, the disclosure with regard to steps (a), (b), (g), and (h) applies to steps (i), (ii), (v), and (vi).

Step (i) of the methods described herein involve contacting yerba mate biomass with an aqueous composition to obtain an initial extract comprising at least one of caffeic acid, monocaffeoylquinic acids, and dicaffeoylquinic acids, and salts thereof.

The aqueous composition can comprise water and not contain any co-solvents, such as organic solvents. But the aqueous composition can comprise co-solvents, in addition to water. Suitable co-solvents include organic solvents, such as, $(C_1$-$C_4)$alkanols and mixtures of $(C_1$-$C_4)$alkanols. The proportion of organic solvent, such as $(C_1$-$C_4)$alkanol or mixtures of $(C_1$-$C_4)$alkanols, can be any suitable proportion such that the aqueous composition can comprise up to about 30%, up to about 40%, up to about 50% or up to about 60% by volume organic solvent, the balance being water; or from about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively, pure water made basic to pH 7-11 with hydroxide, such as sodium or potassium hydroxide can be useful in the aqueous composition, with or without a co-solvent. In still other instances, it may be suitable to add a suitable non-ionic solute that can help balance the osmotic potential of the aqueous composition.

The yerba mate biomass can be stirred, sonicated or otherwise agitated prior to and/or during the contacting of step (i) to, among other things, maximize the extraction of the at least one of caffeic acid, monocaffeoylquinic acids, and dicaffeoylquinic acids, and salts thereof.

The initial extract can be carried through to step (iii) as-is or bulk solids and or plant solids present, such as comminuted yerba mate plant leaves, stalks, tops, roots, and the like, can be removed in step (ii) of the methods described herein. When step (ii) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of caffeic acid, monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Prior to carrying out step (iii) one can optionally adjust the pH of the initial or second initial extract with a suitable acid. (e.g., hydrochloric acid and the like) or suitable base (e.g., sodium hydroxide) to a pH of between about 4 and about 7. The pH-adjusted initial or second initial extract is then extracted with ethyl acetate that has not been pre-acidified as described herein. While not wishing to be bound by any specific theory, it is believed that when the pH of the initial or second initial extract is adjusted to between about 4 and about 7, it is possible to extract certain impurities into the ethyl acetate, while keeping compounds of interest (e.g., caffeic acid, monocaffeoylquinic acids, and dicaffeoylquinic acids, and salts thereof) in the aqueous layer.

Step (iii) of the methods described herein involves contacting the first or second initial extract with acidified ethyl acetate to obtain an acidic ethyl acetate extract. The acidified ethyl acetate can be prepared in any suitable manner, including by adding any suitable acid, including hydrochloric acid, sulfuric acid, and glacial acetic acid (e.g., 0.01-1% vol/vol). The acidic ethyl acetate extract is washed with water (e.g., three times, with 1:1 vol/vol water). Under these conditions, the at least one of caffeic acid, monocaffeoylquinic acids, and dicaffeoylquinic acids will substantially be in their conjugate acid form and will reside substantially in the acidic ethyl acetate layer that forms when the acidic ethyl acetate extract is washed with water. The water layers are discarded and the acidic ethyl acetate extract is carried on to step (iv).

Step (iii) of the methods described herein can be carried out in other suitable ways, including by using ethyl acetate that has not been pre-acidified as described herein (e.g., by pre-washing with glacial acetic acid), but instead by adjusting the pH of the initial or second initial extract with a suitable acid. (e.g., hydrochloric acid and the like), then extracting the pH-adjusted initial or second initial extract with ethyl acetate that has not been pre-acidified. Regardless of the acid used to adjust the pH of the initial extract or the second initial extract, the pH of the initial extract or the second initial extract is adjusted to about 4 or less, 3 or less, about 2 or less, or about 1 or less. The water layers are discarded and the acidic ethyl acetate extract that results is carried on to step (iv).

Step (iv) of the methods described herein involves neutralizing the acidic ethyl acetate extract to obtain neutralized ethyl acetate and an aqueous extract. This is accomplished in any suitable way, including washing the acidic ethyl acetate extract with water (e.g., three times, with 1:1 vol/vol water) comprising a suitable base, such as sodium hydroxide, potassium hydroxide, and the like, and combinations thereof. Under these conditions, the at least one of caffeic acid, monocaffeoylquinic acids, and dicaffeoylquinic acids will substantially be in their conjugate base form and will substantially reside in the water layer that forms when the acidic ethyl acetate extract is washed with water comprising a suitable base.

In an alternative, optional step to step (iv), step (iv-a), the acidic ethyl acetate extract that results from step (iii) can be optionally removed, even removed to dryness. Any solid that remains can either be reconstituted with pH neutral water (e.g., deionized water) and the pH of the water can then be adjusted to about 3 to about 7; or the solid that remains can be reconstituted with water having a pH of about 3 to about 7.

The aqueous extract comprising the at least one of caffeic acid, monocaffeoylquinic acids, and dicaffeoylquinic acids, and salts thereof, whether they emanate from step (iv) or step (iv-a), can then be submitted for step (v) to accomplish, among other things, decoloring of aqueous extract, which can be highly colored. Decoloring can be accomplished by any suitable means, including ultrafiltration (e.g., filtering through a molecular weight cutoff membrane, size-exclusion chromatography, or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the yerba mate biomass or form at one or more of the steps described herein.

Another example of modifications to the method described herein comprising steps (i)-(vi) (including the alternative, optional step (iv-a)) includes a method for making a composition comprising at least one of caffeic acid, monocaffeoylquinic acids, and dicaffeoylquinic acids, and salts thereof, the method comprising
contacting yerba mate biomass with an aqueous composition to obtain an initial extract;
removing solids from the initial extract to obtain a second initial extract;
adjusting the pH of the second initial extract to a pH of from about 4 to about 7 to obtain a first pH-adjusted second initial extract;
contacting the first pH-adjusted second initial extract with ethyl acetate to obtain a first ethyl acetate extract and a second aqueous extract;
adjusting the pH of the second aqueous extract to a pH of less than 2 to obtain a pH-adjusted second aqueous extract;
contacting the pH-adjusted second aqueous extract with ethyl acetate to obtain a second ethyl acetate extract;
removing the ethyl acetate from the second ethyl acetate extract to obtain a purified composition;
reconstituting the crude composition with water to obtain a third aqueous extract; and
decoloring the third aqueous extract to obtain a decolored aqueous extract. The "purified composition" will comprise the compounds of interest (e.g., the at least one of caffeic acid, monocaffeoylquinic acids, and dicaffeoylquinic acids, and salts thereof) and is purified relative to at least the initial extract and the second initial extract, in that the "purified composition" will not contain certain impurities in the initial extract and the second initial extract, but does contain highly colored polymeric substances that either natively exist in the yerba mate biomass or form at one or more of the steps described herein and that are removed in the decoloring step.

Yet another example of modifications to the method described herein comprising steps (i)-(vi) (including the alternative, optional step (iv-a)) includes a method for making a composition comprising at least one of caffeic acid, monocaffeoylquinic acids, and dicaffeoylquinic acids, and salts thereof, the method comprising
contacting yerba mate biomass with an aqueous composition to obtain an initial extract;
removing solids from the initial extract to obtain a second initial extract;
adjusting the pH of the second initial extract to a pH of less than about 2 to obtain a second pH-adjusted second initial extract;
contacting the second pH-adjusted second initial extract with ethyl acetate to obtain a third ethyl acetate extract;
neutralizing the third ethyl acetate extract to obtain a first neutralized ethyl acetate extract and a third aqueous extract; and
decoloring the third aqueous extract to obtain a decolored aqueous extract.

The methods described herein can include step (vi) that involves drying the decolored aqueous extract to obtain the composition comprising the at least one of caffeic acid, monocaffeoylquinic acids, and dicaffeoylquinic acids, and salts thereof. The first or second retentates or the third filtrate can be dried in any suitable manner, including by lyophilization or spray drying.

FIG. 3 is a flow diagram of a method 300 for making a composition comprising at least one of caffeic acid, monocaffeoylquinic acids, and dicaffeoylquinic acids, and salts thereof. In operation 302, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 304, the initial extract is filtered using, for example, a ceramic Büchner funnel with Whatman 54 low ash filter paper into glass 4 L side arm flask to, among other things, remove solids from, e.g., the yerba mate biomass. The filtrate from operation 304 is extracted in operation 306 with acidified ethyl acetate extraction. Following extraction of the at least one of caffeic acid, monocaffeoylquinic acids, and dicaffeoylquinic acids into the acidified ethyl acetate, the acidified ethyl acetate is washed with water comprising a suitable base, such as sodium hydroxide, potassium hydroxide, and the like, in operation 308 to obtain neutralized ethyl acetate and an aqueous extract. Under these conditions, the at least one of caffeic acid, monocaffeoylquinic acids, and dicaffeoylquinic acids will substantially be in their conjugate base form and will substantially reside in the water layer that forms when the acidic ethyl acetate extract is washed with water comprising a suitable base. In operation 310 the water layer is filtered to obtain a filtrate. In operation 316, the filtrate is decolored using a 3 kDa molecular weight cutoff membrane (TURBOCLEAN® NP010; six diafiltrations) to, among other things, decolor the aqueous extract, thereby obtaining a decolored aqueous extract. In operation 320, the decolored aqueous extract is dried to obtain the composition at least one of caffeic acid, monocaffeoylquinic acids, and dicaffeoylquinic acids, and salts thereof.

FIG. 4 is a flow diagram of a method 400 for making a composition comprising at least one of caffeic acid, monocaffeoylquinic acids, and dicaffeoylquinic acids, and salts thereof. In operation 402, yerba mate biomass is contacted with an aqueous composition containing 50% ethanol/water in a suitable container (e.g., a glass jar) for 1 h (300 g yerba mate biomass into 1.5 L solvent) to obtain an initial extract.

In operation 404, the initial extract is filtered using, for example, a ceramic Büchner funnel with Whatman 54 low ash filter paper into glass 4 L side arm flask to, among other things, remove solids from, e.g., the yerba mate biomass. The filtrate from operation 404 is pH-adjusted to from about 4 to about 7 and the filtrate is extracted in operation 408 with ethyl acetate, while the compounds of interest remain in the aqueous layer. In operation 406, the pH of the aqueous layer is adjusted to less than 2 and the aqueous layer is extracted with ethyl acetate. Following extraction of the at least one of caffeic acid, monocaffeoylquinic acids, and dicaffeoylquinic acids into the ethyl acetate, the ethyl acetate is removed to dryness in operation 407 to obtain a solid. The solid is reconstituted with water and the pH of the water is adjusted to from about 3 to about 7. Under these conditions, the at least one of caffeic acid, monocaffeoylquinic acids, and dicaffeoylquinic acids will substantially be in their conjugate base form and will dissolve in the water. In operation 410 the water layer is filtered to obtain a filtrate. In operation 416, the filtrate is decolored using a 3 kDa molecular weight cutoff membrane (TURBOCLEAN® NP010; six diafiltrations) to, among other things, decolor the aqueous extract, thereby obtaining a decolored aqueous extract. In operation 420, the decolored aqueous extract is dried to obtain the composition at least one of caffeic acid, monocaffeoylquinic acids, and dicaffeoylquinic acids, and salts thereof.

The composition comprising the at least one of caffeic acid, monocaffeoylquinic acids, and dicaffeoylquinic acids, and salts thereof prepared according to the methods described herein can comprise substantially the same amounts by weight and/or substantially the same ratios by weight of caffeic acid, monocaffeoylquinic acids, and dicaffeoylquinic acids, and salts thereof relative to the yerba mate biomass.

The composition comprising the at least one of caffeic acid, monocaffeoylquinic acids, and dicaffeoylquinic acids, and salts thereof prepared according to the methods described herein can comprise a ratio by mass of total dicaffeoylquinic acids to total monocaffeoylquinic acids of about 1:1 to about 10:1 (e.g., from about 3:1 to about 10:1; about 3:2 to about 4:1; or about 3:1 to about 5:1). The composition comprising the at least one of caffeic acid, monocaffeoylquinic acids, and dicaffeoylquinic acids, and salts thereof prepared according to the methods described herein can comprise a ratio by mass of total dicaffeoylquinic acids to total monocaffeoylquinic acids of from about 1:1 to about 0.01:1 (e.g., from about 0.5:1 to about 0.1:1).

The composition comprising the at least one of caffeic acid, monocaffeoylquinic acids, and dicaffeoylquinic acids, and salts thereof prepared according to the methods described herein can comprise a ratio by mass of each one of caffeic acid, monocaffeoylquinic acids, and dicaffeoylquinic acids, and salts thereof, of about 0.01 (e.g., about 0.005 to about 0.05) to about 1 (e.g., 0.5 to about 1.5) to about 1 (e.g., 0.5 to about 1.5), respectively.

The composition comprising the at least one of caffeic acid, monocaffeoylquinic acids, and dicaffeoylquinic acids, and salts thereof prepared according to the methods described herein can be incorporated into any ingestible composition, including into beverages and food products.

For example, the ingestible composition can be a comestible composition or noncomestible composition. By "comestible composition", it is meant any composition that can be consumed as food by humans or animals, including solids, gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical compositions, which refers to a noncomestible composition intended to be used by humans or animals for therapeutic purposes. By "animal", it includes any non-human animal, such as, for example, farm animals and pets.

The composition comprising the at least one of caffeic acid, monocaffeoylquinic acids, and dicaffeoylquinic acids, and salts thereof prepared according to the methods described herein can be added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as lip balms and other personal care products.

In general, over the counter (OTC) product and oral hygiene product generally refer to product for household and/or personal use which may be sold without a prescription and/or without a visit to a medical professional. Examples of the OTC products include, but are not limited to Vitamins and dietary supplements; Topical analgesics and/or anaesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anaesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene products include, but are not limited to mouth cleaning strips, toothpaste, toothbrushes, mouthwashes/dental rinses, denture care, mouth fresheners at-home teeth whiteners and dental floss.

The composition comprising the at least one of caffeic acid, monocaffeoylquinic acids, and dicaffeoylquinic acids, and salts thereof prepared according to the methods described herein can be added to food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready to serve, semi condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready to cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category means beverages, beverage mixes and concentrates, including but not limited to, carbonated and non-carbonated beverages, alcoholic and nonalcoholic beverages, ready to drink beverages, liquid concentrate formulations for preparing beverages such as sodas, and dry powdered beverage precursor mixes. The Beverage category also include the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh (e.g., brewed), instant, combined coffee, liquid, ready-to-drink, soluble and dry coffee beverages, coffee beverage mixes and concentrates (syrups, pure, formulated, or in powder form; example of a "powder form" is a product comprising coffee, sweetener, and whitener all in powder form); tea, such as black, green, white, oolong, and flavored tea; and other hot drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products. The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The read meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi pack dairy ice cream, multi pack water ice cream, take home ice cream, take home dairy ice cream, ice cream desserts, bulk ice cream, take home water ice cream, frozen yoghurt, artisanal ice cream, dairy products, milk, fresh/pasteurized milk, full fat fresh/pasteurized milk, semi skimmed fresh/pasteurized milk, long life/uht milk, full fat long life/uht milk, semi skimmed long life/uht milk, fat free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners (e.g., dairy and non-dairy based creamers or whiteners for coffee beverages), powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf stable desserts, dairy based desserts, soy based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars; energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow on milk formula, toddler milk formula, hypoallergenic milk formula, prepared baby food, dried baby food, other baby food, spreads, jams and preserves, honey, chocolate spreads, nut based spreads, and yeast-based spreads. Examples of comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Examples of comestible compositions also include breakfast cereals, sweet beverages or solid or liquid concentrate compositions for preparing beverages. Examples of comestible compositions also include coffee flavored food (e.g., coffee flavored ice cream).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

EXAMPLES

The present invention can be better understood by reference to the following examples which are offered by way of illustration. The present invention is not limited to the examples given herein.

Materials and Methods

A yerba mate biomass that can be used is a commercially-available product sold as ECOTEAS™ Yerba Mate Unsmoked Leaf and Stem Traditional Cut, which is yerba mate tea grown in the state of Misiones in northeastern Argentina. The biomass is obtained already comminuted. A portion of the comminuted yerba mate biomass (300 g) was suspended in 50% ethanol/water (1.5 L) in glass jar and was shaken for 1 hour. After shaking, the resulting mixture was filtered using a ceramic Büchner funnel with Whatman 54 low ash filter paper into glass 4 L side arm flask. The filtered material was diluted to 35% ethanol using water. Upon dilution, some unwanted material precipitates, as it is not soluble at 35% by volume ethanol. The diluted material was therefore re-filtered using a ceramic Büchner funnel with Whatman 44 low ash filter paper into glass 4 L side arm flask.

AMBERLITE® FPA 53 resin in a glass column was prepared for ion exchange chromatography by treating the resin with aqueous hydrochloric acid to protonate amines in the resin. Chloride is then washed off until the pH is greater than 4 with approximately 10 BV of water. The resin is then pre-conditioned with 35% ethanol in water (2 BV at 2 BV/h) prior to loading. The re-filtered material was loaded onto the resin. The loading permeate was discarded. The resin was then washed with 35% ethanol in water (4 BV at 2 BV/h). The permeate was discarded. The resin was then eluted with 50% ethanol in water, comprising 10% FCC sodium chloride (4 BV, 0.5 BV/h). This last permeate was taken to the next step, where the solvent was removed slowly by blowing nitrogen gas over top of the permeate for two days, until volume was approximately ⅓ of initial volume and/or the ethanol concentration was <1% of the solution. The temperature was kept at ambient (about 25° C.) temperature or below, as high temperatures, high oxygen content, and/or high exposure to light can degrade the compounds of interest. If such care is not taken, the compounds will polymerize to form highly colored, hydrophobic polymers, some of the largest of which are insoluble in water.

The concentrated material was filtered through Whatman 44 filter paper on a Büchner funnel followed by filtering through an 0.2 μm polyethersulfone filter. The filtered material was decolored using a 3 kDa molecular weight cutoff membrane TURBOCLEAN® NP010, keeping the permeate, although a GE Osmonic Sepa CF TF (thin film) UF GK membrane can be used. The decolored material will degrade/polymerize over time and can degrade due to oxidation processes, and this will re-introduce color into the system. It is therefore advisable to desalt and dry shortly after decoloring, such as within one to two days. The decolored material was then filtered through a TRISEP® XN45 nanofiltration membrane to desalt. The desalted material was freeze-dried using LABCONCO™ FAST-FREEZE™ 600 mL flasks.

The freeze-dried material was characterized using UHPLC-UV analysis using a C18-based reversed-phase column. The mobile phase A consists of 0.025% TFA in water and mobile phase B is acetonitrile. After an initial hold at 5% B, the compounds are eluted at elevated temperature by a gradient from 5% B to 25% B from 1.2 to 15 minutes at a flow rate of 0.4 mL/min. The column is then washed with 100% acetonitrile and re-equilibrated. The UV detector is set to record data at 210 and 324 nm.

Figure 5:
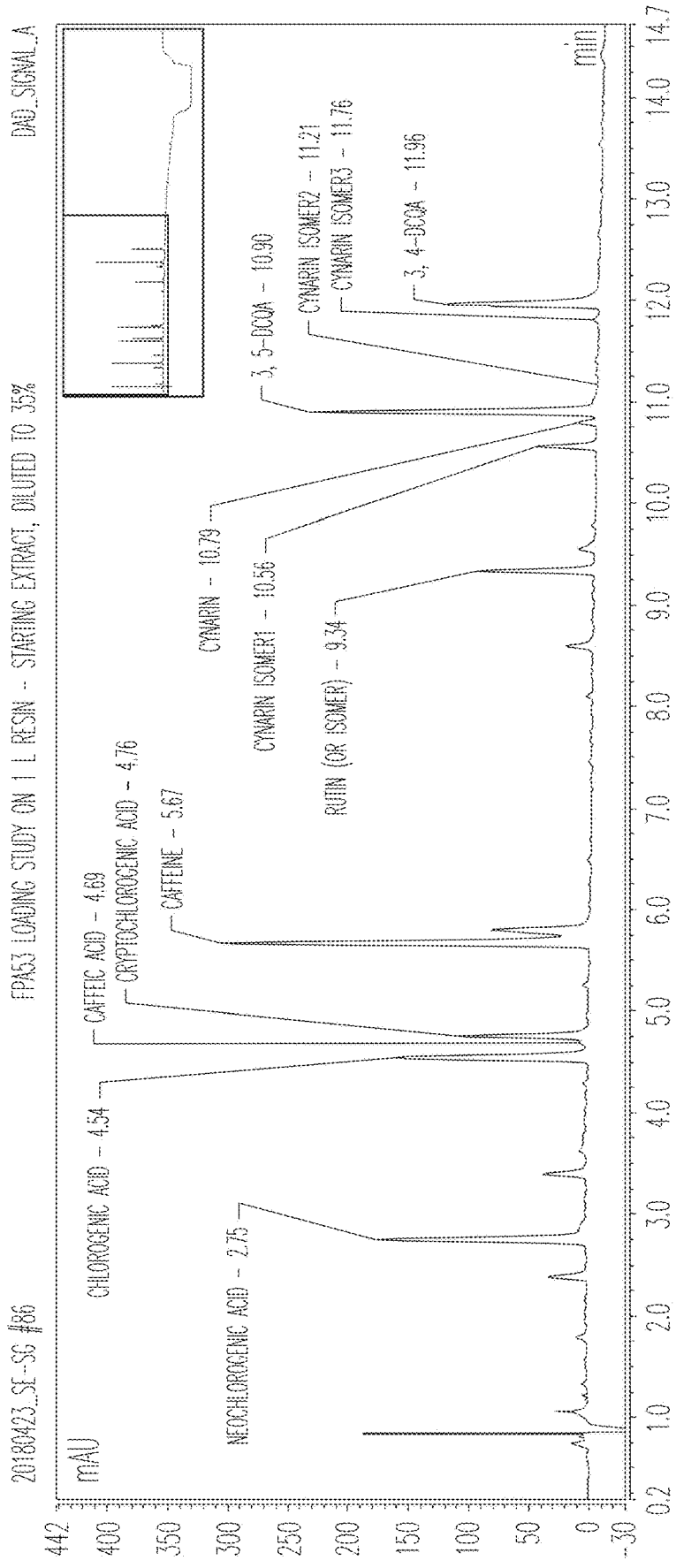
FIGS. 5-7 are UHPLC-UV chromatograms of an initial yerba mate extract, a concentrate obtained following chromatographing the adjusted second initial extract on an ion exchange chromatography stationary phase; and after drying, following the process described in steps (a)-(h), described herein, where "DCQA" refers to "dicaffeoylquinic acid."
Figure 6:
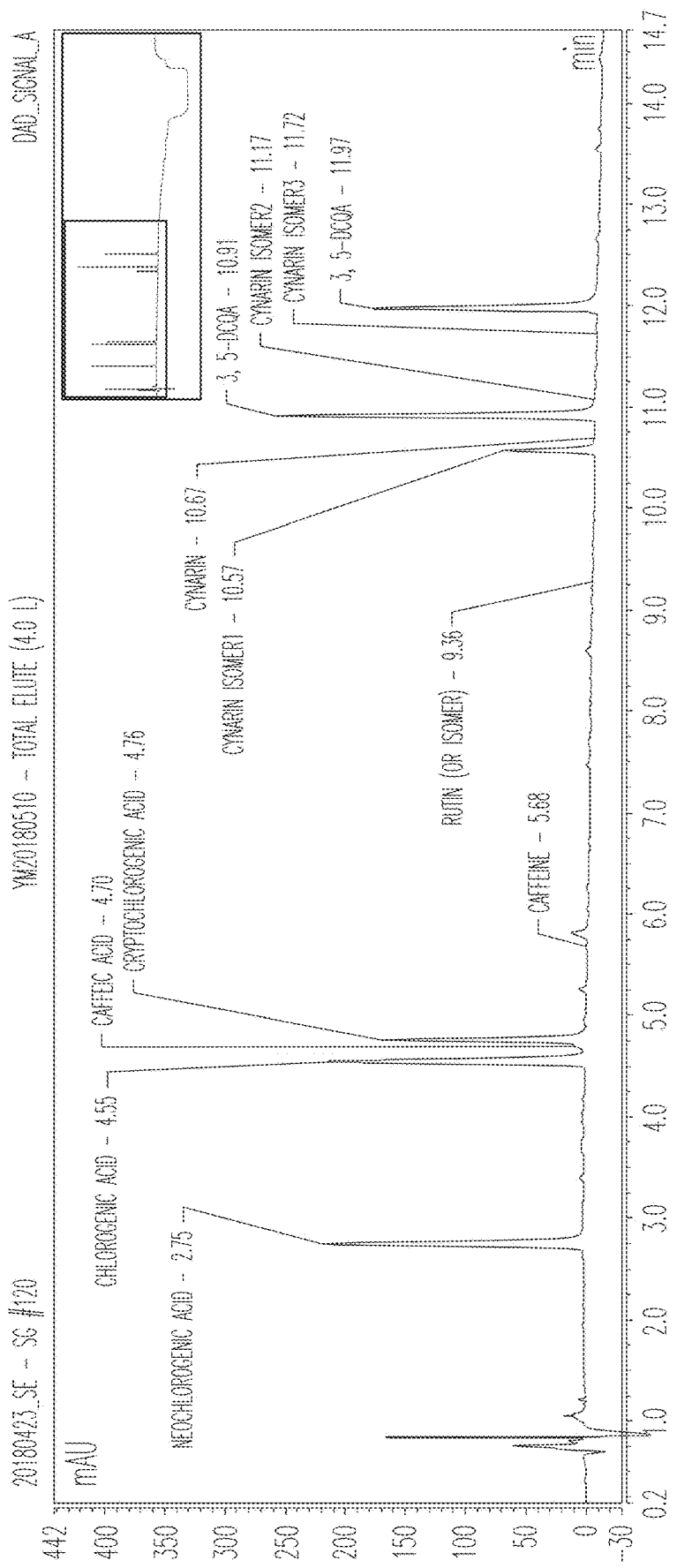
Figure 7:
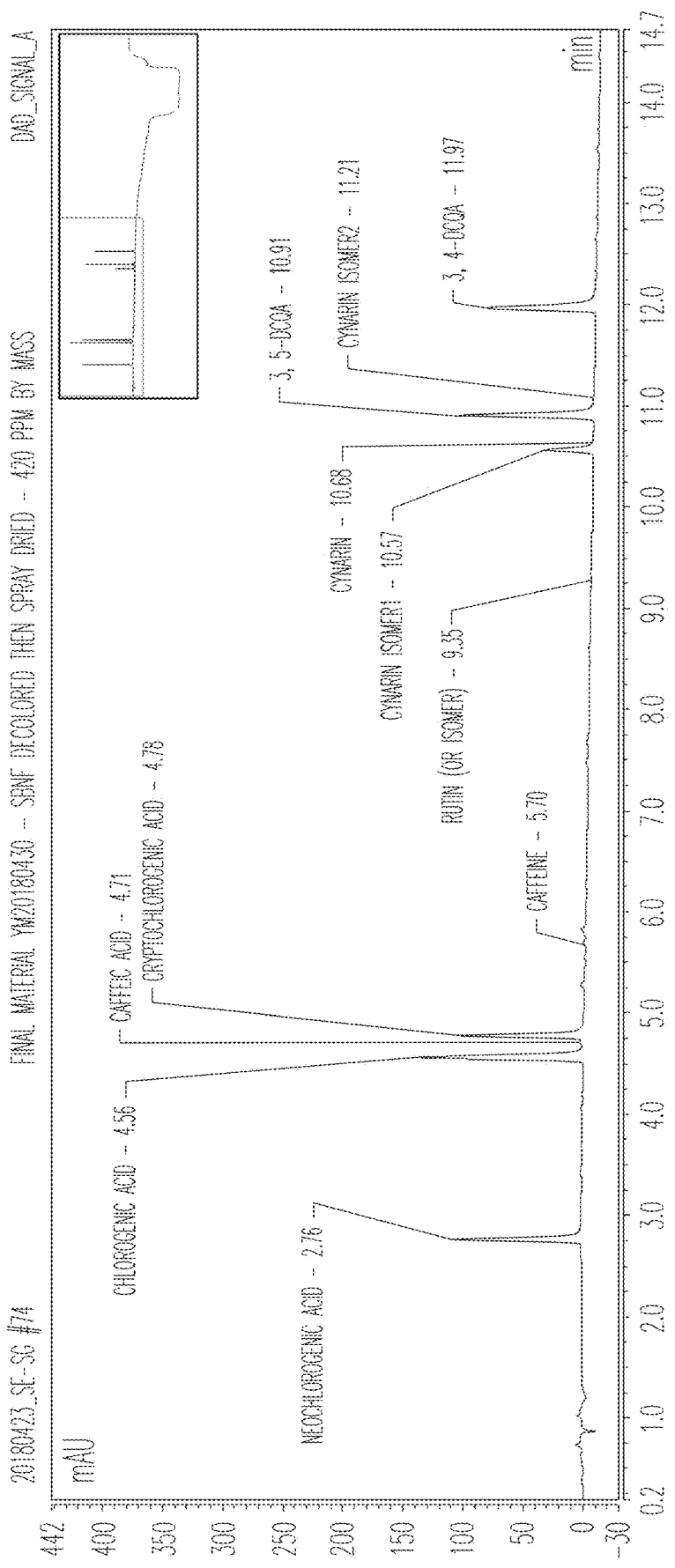

FIGS. 5-7 are UHPLC-UV chromatograms of an initial yerba mate extract, a concentrate obtained following chromatographing the adjusted second initial extract on an ion exchange chromatography stationary phase; and after drying, following the process described in steps (a)-(h), where "DCQA" refers to "dicaffeoylquinic acid." FIG. 5 shows that the initial yerba mate extract contains caffeine and rutin, in addition to the compounds of interest, including chlorogenic acid, neochlorogenic acid, cryptochlorogenic acid, caffeic acid, and the various isomers of dicaffeoylquinic acids, including 3,4-DCQA and 3,5-DCQA. As described herein, and as shown in FIG. 6, the chromatographing removes a large amount of the caffeine and ruting present in the initial yerba mate extract. The peaks at a retention time of approximately 5.67 minutes, corresponding to caffeine, and at approximately 9.36 minutes, corresponding to rutin, present in FIG. 5 are absent in FIG. 6. The same holds true in FIG. 7. It is worth noting that the relative intensities of the peaks for neochlorogenic acid, chlorogenic acid, caffeic acid, cryptochlorogenic acid, and the various isomers of dicaffeoylquinic acid are persevered, thus lending credence to the fact that the compositions obtained using the methods described herein comprises substantially the same amounts by weight or substantially the same ratios by weight of caffeic acid, monocaffeoylquinic acids, and dicaffeoylquinic acids, and salts thereof relative to the yerba mate biomass.

FIGS. 8-10 are tables showing, in tabular form, the peak name, retention time, and relative area percent data for the UHPLC-UV chromatographs shown in FIGS. 5-7, respectively.

The present invention provides for the following embodiments, the numbering of which is not to be construed as designating levels of importance:

Embodiment 1 relates to a method for making a composition comprising at least one of caffeic acid, monocaffeoylquinic acids, and dicaffeoylquinic acids, and salts thereof, the method comprising: contacting yerba mate biomass with a first aqueous composition to obtain an initial extract; adjusting the volume of the initial extract with a second aqueous composition to obtain an adjusted initial extract; chromatographing the adjusted initial extract on an ion exchange stationary phase; eluting the stationary phase to obtain a first eluent comprising a solvent; removing the solvent to form a concentrate; and at least one of decoloring and desalting the concentrate to at least one of a filtrate and a retentate.

Embodiment 2 relates to the method of Embodiment 1, further comprising removing solids from the initial extract to obtain a second initial extract; adjusting the volume of the second initial extract with a second aqueous composition to obtain an adjusted second initial extract; and chromatographing the adjusted second initial extract on an ion exchange stationary phase.

Embodiment 3 relates to the method of Embodiments 1-2, further comprising drying the at least one of a filtrate and a retentate to obtain the composition comprising at least one of caffeic acid, monocaffeoylquinic acids, and dicaffeoylquinic acids, and salts thereof.

Embodiment 4 relates to the method of Embodiments 1-3, wherein the drying comprises lyophilization or spray drying.

Embodiment 5 relates to the method of Embodiments 1-4, wherein the yerba mate biomass comprises at least one of yerba mate leaves and yerba mate stems.

Embodiment 6 relates to the method of Embodiments 1-5, wherein the at least one of the yerba mate biomass is comminuted prior to the contacting.

Embodiment 7 relates to the method of Embodiments 1-6, wherein the adjusting the volume of the initial extract or the second initial extract with the second aqueous composition to obtain an adjusted initial extract or adjusted second initial extract comprises adjusting the initial extract or second initial extract with a sufficient amount of the second aqueous composition to obtain an adjusted initial extract or adjusted second initial extract comprising from about 30% to about 40% by volume of an organic solvent.

Embodiment 8 relates to the method of Embodiment 7, wherein the second aqueous composition is water.

Embodiment 9 relates to the method of Embodiments 1-8, further comprising filtering the adjusted initial extract or second initial extract prior to the chromatographing.

Embodiment 10 relates to the method of Embodiments 1-9, wherein the eluting comprises eluting with a solution comprising a salt.

Embodiment 11 relates to the method of Embodiment 10, wherein the solution comprising a salt comprises at least one salt dissolved in an aqueous composition comprising a $(C_1-C_4)$alkanol.

Embodiment 12 relates to the method of Embodiment 10, wherein the salt solution comprises sodium chloride, potassium chloride, and mixtures thereof.

Embodiment 13 relates to the method of Embodiments 1-12, further comprising adjusting the pH of the weak ion exchange stationary phase prior to the chromatographing such that the pH of the ion exchange stationary phase is a pH of less than about 10.

Embodiment 14 relates to the method of Embodiments 1-13, further comprising pre-conditioning the ion exchange stationary phase with an aqueous composition comprising 30% to about 40% by volume of a $(C_1-C_4)$alkanol.

Embodiment 15 relates to the method of Embodiments 1-14, wherein the first eluent is concentrated to about 30% of an original, total volume of the first eluent or until a concentration of $(C_1-C_4)$alkanol in the eluent is less than about 2% by volume.

Embodiment 16 relates to the method of Embodiments 1-15, wherein the decoloring is performed before the desalting.

Embodiment 17 relates to the method of Embodiments 1-15, wherein the desalting is performed before the decoloring.

Embodiment 18 relates to the method of Embodiments 1-17, wherein the decoloring comprises ultrafiltration through a molecular weight cutoff membrane, size-exclusion chromatography or gel permeation.

Embodiment 19 relates to the method of Embodiments 1-18, wherein the desalting comprises using nanofiltration membrane or a hydrophobic resin.

Embodiment 20 relates to the method of Embodiments 1-19, wherein the concentrate is filtered through filter paper to obtain a first filtrate, the first filtrate is ultrafiltered to obtain a second filtrate, and the second filtrate is nanofiltered using a nanofiltration membrane to obtain a first retentate or the second filtrate is eluted through a hydrophobic resin to obtain a desalted second eluent.

Embodiment 21 relates to the method of Embodiments 1-20, wherein the concentrate is filtered through filter paper to obtain a first filtrate, the first filtrate is nanofiltered using a nanofiltration membrane to obtain a third retentate or the first filtrate is eluted through a hydrophobic resin to obtain a desalted second eluent, and the third retentate or the desalted second eluent is ultrafiltered to obtain a third filtrate.

Embodiment 22 relates to the method of Embodiments 1-21, wherein at least one of the removing the solvent; and the decoloring/desalting are performed under an inert atmosphere.

Embodiment 23 relates to the method of Embodiments 1-22, wherein the $(C_1-C_4)$alkanol is ethanol.

Embodiment 24 relates to the method of Embodiments 1-22, wherein the composition comprises substantially the same amounts by weight or substantially the same ratios by weight of caffeic acid, monocaffeoylquinic acids, and dicaffeoylquinic acids, and salts thereof relative to the yerba mate biomass.

Embodiment 25 relates to method of Embodiments 1-24, wherein the composition comprises a ratio by mass of total dicaffeoylquinic acids to total monocaffeoylquinic acids of about 1:1 to about 10:1.

Embodiment 26 relates to the method of Embodiments 1-25, wherein the composition comprises a ratio by mass of each one of caffeic acid, monocaffeoylquinic acids, and dicaffeoylquinic acids, and salts thereof, of about 0.01 to about 1 to about 1.

Embodiment 27 relates to a method for making a composition comprising at least one of caffeic acid, monocaffeoylquinic acids, and dicaffeoylquinic acids, and salts thereof, the method comprising: contacting yerba mate biomass with an aqueous composition to obtain an initial extract; removing solids from the initial extract to obtain a second initial extract; contacting the second initial extract with acidified ethyl acetate to obtain an acidic ethyl acetate extract; neutralizing the acidic ethyl acetate extract to obtain neutralized ethyl acetate extract and a first aqueous extract; and decoloring the first aqueous extract to obtain a decolored aqueous extract.

Embodiment 28 relates to the method of Embodiment 27, further comprising drying the decolored aqueous extract to obtain the composition comprising at least one of caffeic acid, monocaffeoylquinic acids, and dicaffeoylquinic acids, and salts thereof of.

Embodiment 29 relates to the method of Embodiments 27-28, wherein the yerba mate biomass comprises at least one of yerba mate leaves and stems.

Embodiment 30 relates to the method of Embodiments 27-29, wherein the at least one of the yerba mate biomass is comminuted prior to the contacting.

Embodiment 31 relates to the method of Embodiments 27-30, wherein the composition comprises substantially the same amounts by weight or substantially the same ratios by weight of caffeic acid, monocaffeoylquinic acids, and dicaffeoylquinic acids, and salts thereof relative to the yerba mate biomass.

Embodiment 32 relates to the method of Embodiments 27-31, wherein the composition comprising the at least one of caffeic acid, monocaffeoylquinic acids, and dicaffeoylquinic acids, and salts thereof comprises a ratio by mass of total dicaffeoylquinic acids to total monocaffeoylquinic acids of about 1:1 to about 10:1.

Embodiment 33 relates to the method of Embodiments 27-32, wherein the composition comprising the at least one of caffeic acid, monocaffeoylquinic acids, and dicaffeoylquinic acids, and salts thereof comprises a ratio by mass of each one of caffeic acid, monocaffeoylquinic acids, and dicaffeoylquinic acids, and salts thereof, of about 0.5 to about 1 to about 1.

Embodiment 34 relates to a method for making a composition comprising at least one of caffeic acid, monocaffeoylquinic acids, and dicaffeoylquinic acids, and salts thereof, the method comprising: contacting yerba mate biomass with an aqueous composition to obtain an initial extract; removing solids from the initial extract to obtain a second initial extract; adjusting the pH of the second initial extract to a pH of from about 4 to about 7 to obtain a first pH-adjusted second initial extract; contacting the first pH-adjusted second initial extract with ethyl acetate to obtain a first ethyl acetate extract and a second aqueous extract; adjusting the pH of the second aqueous extract to a pH of less than 2 to obtain a pH-adjusted second aqueous extract; contacting the pH-adjusted second aqueous extract with ethyl acetate to obtain a second ethyl acetate extract; removing the ethyl acetate from the second ethyl acetate extract to obtain a crude composition; reconstituting the crude composition with water to obtain a third aqueous extract; and decoloring the third aqueous extract to obtain a decolored aqueous extract.

Embodiment 35 relates to a method for making a composition comprising at least one of caffeic acid, monocaffeoylquinic acids, and dicaffeoylquinic acids, and salts thereof, the method comprising: contacting yerba mate biomass with an aqueous composition to obtain an initial extract; removing solids from the initial extract to obtain a second initial extract; adjusting the pH of the second initial extract to a pH of less than about 2 to obtain a second pH-adjusted second initial extract; contacting the second pH-adjusted second initial extract with ethyl acetate to obtain a third ethyl acetate extract; neutralizing the third ethyl acetate extract to obtain a first neutralized ethyl acetate extract and a third aqueous extract; and decoloring the third aqueous extract to obtain a decolored aqueous extract.

Embodiment 36 relates to a composition comprising at least one of caffeic acid, monocaffeoylquinic acids, and dicaffeoylquinic acids, and salts thereof made by the method of Embodiments 1-35.

Embodiment 37 relates to an ingestible composition comprising the composition of Embodiment 36.

Embodiment 38 relates to the ingestible composition of Embodiment 37, wherein the ingestible composition is a beverage or a food product.

What is claimed is:
1. A method for making a yerba mate extract composition comprising at least one of caffeic acid, monocaffeoylquinic acids, and dicaffeoylquinic acids, and salts thereof and less than 1% by weight of at least one of caffeine, rutin, and rutin isomers, the method comprising:

contacting yerba mate biomass with a first aqueous organic solvent composition comprising 30% to 60% $(C_1\text{-}C_4)$alkanol to obtain an initial extract;

adjusting the volume of the initial extract with a second aqueous composition to obtain an adjusted initial extract comprising less than 40% $(C_1\text{-}C_4)$alkanol;

chromatographing the adjusted initial extract on an ion exchange stationary phase;

eluting an eluent from the stationary phase with a third solvent comprising 40% to 60% $(C_1\text{-}C_4)$alkanol;

removing the third solvent from the eluent to form a concentrate; and at least one of decoloring and desalting the concentrate to form the yerba mate extract composition comprising at least one of caffeic acid, monocaffeoylquinic acids, dicaffeoylquinic acids, and salts thereof and less than 1% by weight of at least one of caffeine, rutin, and rutin isomers.

2. The method of claim 1, additionally comprising the step of removing solids from the initial extract prior to adjusting the volume.

3. The method of claim 1, additionally comprising the step of washing the ion exchange stationary phase with a fourth aqueous organic solvent composition comprising 10% to 40% $(C_1\text{-}C_4)$alkanol prior to eluting the eluent.

4. The method of claim 1, wherein the third solvent is removed until the $(C_1\text{-}C_4)$alkanol concentration is less than 1%.

5. The method of claim 1, wherein the solvent is removed by evaporation.

6. The method of claim 1, wherein the yerba mate extract composition comprises less than 0.5% by mass of at least one of caffeine, rutin, and rutin isomers.

7. The method of claim 1, wherein the yerba mate extract composition comprises less than 0.1% by weight of caffeine, rutin, and rutin isomers combined.

8. The method of claim 1, wherein the yerba mate extract composition is free of caffeine, rutin, and rutin isomers.

9. The method of claim 1, wherein the third solvent additionally comprises about 5 wt % to about 25 wt % of a salt.

10. The method of claim 1, wherein the yerba mate extract composition comprises greater than 80% by weight of the total of caffeic acid, monocaffeoylquinic acids, dicaffeoylquinic acids, and salts thereof.

11. The method of claim 1, wherein the yerba mate extract composition comprises a ratio by mass of total dicaffeoylquinic acids and salts thereof to total monocaffeoylquinic acids and salts thereof of about 1:1 to about 10:1.

12. The method of claim 1, wherein the yerba mate extract composition comprises at least one of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

13. The method of claim 1, wherein the yerba mate extract composition comprises at least one of chlorogenic acid, neochlorogenic acid, and cryptochlorogenic acid, and salts thereof.

14. A method for making a yerba mate extract composition comprising at least one of caffeic acid, monocaffeoylquinic acids, dicaffeoylquinic acids, and salts thereof, the method comprising:

contacting yerba mate biomass with a first aqueous organic solvent composition comprising 30% to 60% $(C_1\text{-}C_4)$alkanol to obtain an initial extract;

removing solids from the initial extract;
adjusting the volume of the initial extract with a second aqueous composition to obtain an adjusted initial extract comprising less than 40% $(C_1-C_4)$alkanol;
loading the adjusted initial extract on an ion exchange stationary phase;
washing the loaded ion exchange stationary phase with a third aqueous organic solvent composition comprising 10% to 40% $(C_1-C_4)$alkanol
eluting an eluent from the loaded, washed stationary phase with a fourth solvent comprising 40% to 60% $(C_1-C_4)$alkanol;
removing the fourth solvent from the eluent to form a concentrate; and
at least one of decoloring and desalting the concentrate to form the yerba mate extract composition comprising at least 80% by weight of the total of caffeic acid, monocaffeoylquinic acids, dicaffeoylquinic acids, and salts thereof, and less than 1% by weight of at least one of caffeine, rutin, and rutin isomers.

15. The method of claim 14, wherein the fourth solvent is removed until the $(C_1-C_4)$alkanol concentration is less than 1%.

16. The method of claim 14, wherein the solvent is removed by evaporation.

17. The method of claim 14, wherein the yerba mate extract composition comprises less than 0.5% by mass of at least one of caffeine, rutin, and rutin isomers.

18. The method of claim 14, wherein the yerba mate extract composition comprises less than 0.1% by weight of caffeine, rutin, and rutin isomers combined.

19. The method of claim 14, wherein the yerba mate extract composition is free of caffeine, rutin, and rutin isomers.

20. The method of claim 14, wherein the third solvent additionally comprises about 5 wt % to about 25 wt % of a salt.

21. The method of claim 14, wherein the yerba mate extract composition comprises a ratio by mass of total dicaffeoylquinic acids and salts thereof to total monocaffeoylquinic acids and s of about 1:1 to about 10:1.

22. The method of claim 14, wherein the yerba mate extract composition comprises at least one of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

23. The method of claim 14, wherein the yerba mate extract composition comprises at least one of chlorogenic acid, neochlorogenic acid, and cryptochlorogenic acid, and salts thereof.

24. The method of claim 9, wherein the salt comprises at least one of sodium chloride, potassium chloride, ammonium chloride, sodium sulfate, potassium sulfate, sodium phosphate, and potassium phosphate.

25. The method of claim 20, wherein the salt comprises at least one of sodium chloride, potassium chloride, ammonium chloride, sodium sulfate, potassium sulfate, sodium phosphate, and potassium phosphate.

* * * * *